(12) United States Patent
Borgos et al.

(10) Patent No.: US 7,463,796 B2
(45) Date of Patent: Dec. 9, 2008

(54) WAVEGUIDE AND OPTICAL MOTION SENSOR USING OPTICAL POWER MODULATION

(75) Inventors: John A. Borgos, Shoreview, MN (US); Thomas A. Borgos, Lino Lakes, MN (US); Troy Pongratz, Minneapolis, MN (US)

(73) Assignee: Tarilian Laser Technologies, Limited, Hertfordshire (GB)

( * ) Notice: Subject to any disclaimer, the term of this patent is extended or adjusted under 35 U.S.C. 154(b) by 0 days.

(21) Appl. No.: 11/944,029

(22) Filed: Nov. 21, 2007

(65) Prior Publication Data
US 2008/0181556 A1    Jul. 31, 2008

Related U.S. Application Data

(60) Provisional application No. 60/898,269, filed on Jan. 31, 2007, provisional application No. 60/998,745, filed on Oct. 15, 2007.

(51) Int. Cl.
*G02B 6/00* (2006.01)
*G01J 1/56* (2006.01)
(52) U.S. Cl. .................. 385/12; 385/13; 385/88; 250/227.11; 250/227.14; 250/231.19
(58) Field of Classification Search .............. 385/12, 385/13, 14, 88, 92; 250/227.11, 227.14, 250/231.19
See application file for complete search history.

(56) References Cited

U.S. PATENT DOCUMENTS 3,517,999 A    6/1970  Weaver ............... 385/147 X
4,163,397 A    8/1979  Harmer ..................... 73/800
4,297,684 A   10/1981  Butter ..................... 340/557
4,421,979 A   12/1983  Asawa et al. ........... 250/227.11
4,701,017 A *  10/1987  Kookootsedes et al. ..... 385/141

(Continued)

FOREIGN PATENT DOCUMENTS

EP         0348224        6/1989

(Continued)

OTHER PUBLICATIONS

International Search and Written Opinion mailed Dec. 3, 2007 in PCT/US2007/069545, 27 pages.

(Continued)

*Primary Examiner*—Brian M Healy
(74) *Attorney, Agent, or Firm*—Fish & Richardson P.C.

(57) ABSTRACT

An optical motion sensing device included a sensor frame defining an opening, a sensor pad disposed in the opening, an optical sensing system adapted to detect an amount of movement of the sensor pad in the sensor frame, and an output unit. The optical sensing system includes an optical waveguide, an optical source device, and an optical detector. The optical waveguide is positioned within the sensor frame such that the movement of the sensor pad results in the flexing or compressing of the optical waveguide. The optical source device supplies optical energy to the optical waveguide. The optical detector detects an amount of optical energy exiting the optical waveguide. The output unit is configured to receive a signal indicative of the amount of optical energy exiting the optical waveguide and to generate a measure of the amount of movement of the sensor pad from the received signal.

25 Claims, 12 Drawing Sheets

U.S. PATENT DOCUMENTS

| | | | |
|---|---|---|---|
| 4,750,796 A | 6/1988 | Shibata et al. | 385/12 X |
| 4,822,135 A | 4/1989 | Seaver | 385/12 X |
| 4,830,461 A | 5/1989 | Ishiharada et al. | 385/12 X |
| 4,937,029 A | 6/1990 | Ishiharada et al. | 264/1.5 |
| 5,088,501 A * | 2/1992 | Niewisch | 600/534 |
| 5,089,697 A | 2/1992 | Prohaska | 250/227.21 |
| 5,107,847 A | 4/1992 | Knute et al. | 128/675 |
| 5,138,152 A | 8/1992 | Botting | 250/227.16 |
| 5,144,689 A | 9/1992 | Lovely | 385/12 |
| 5,154,680 A | 10/1992 | Drzewiecki et al. | 128/672 |
| 5,158,091 A | 10/1992 | Butterfield et al. | 128/672 |
| 5,183,056 A * | 2/1993 | Dalen et al. | 600/595 |
| 5,212,379 A | 5/1993 | Nafarrate et al. | 250/227.14 |
| 5,241,300 A | 8/1993 | Buschmann | 340/573 |
| 5,276,322 A | 1/1994 | Carome | 250/227.21 |
| 5,291,013 A | 3/1994 | Nafarrate et al. | 250/227.14 |
| 5,436,444 A | 7/1995 | Rawson | 250/227.14 |
| 5,711,291 A | 1/1998 | Takaki | 128/667 |
| 5,840,036 A | 11/1998 | Voith | 600/493 |
| 6,052,613 A | 4/2000 | Takaki | 600/479 |
| 6,490,931 B1 * | 12/2002 | Fernald et al. | 73/705 |
| 6,491,647 B1 | 12/2002 | Bridger et al. | 600/585 |
| 6,498,652 B1 | 12/2002 | Varshneya et al. | 356/477 |
| 6,533,729 B1 | 3/2003 | Khair et al. | 600/503 |
| 6,763,256 B2 * | 7/2004 | Kimball et al. | 600/336 |
| 6,816,266 B2 | 11/2004 | Varshneya et al. | 356/477 |
| 6,820,489 B2 * | 11/2004 | Fernald et al. | 73/705 |
| 2007/0142715 A1 | 6/2007 | Banet et al. | 600/301 |
| 2007/0185393 A1 | 8/2007 | Zhou et al. | 600/323 |
| 2007/0276261 A1 | 11/2007 | Banet et al. | 600/481 |
| 2007/0276262 A1 | 11/2007 | Banet et al. | 600/485 |
| 2007/0276632 A1 | 11/2007 | Banet et al. | 702/187 |
| 2008/0181556 A1 * | 7/2008 | Borgos et al. | 385/13 |

FOREIGN PATENT DOCUMENTS

| | | | |
|---|---|---|---|
| EP | 1484010 | 12/2004 | |
| JP | 08 285709 | 11/1996 | 385/12 X |
| SU | 1219047 | 3/1986 | 385/12 X |
| WO | 96/08197 | 3/1996 | |
| WO | 2008094340 | 8/2008 | 385/12 X |

OTHER PUBLICATIONS

Ulyanov S. et al. "Speckle Interferometry for Biotissue Vibration Measurement" *Optical Engineering*, 1994, 33(3): 908-914.

Hong et al, "Fiber-optic transducer for blood pressure measurements" Nov. 4, 1988, pp. 810-811.

International Search Report in PCT/US2007/085397, mailed Sep. 4, 2008, 17 pages.

Gagnadre et al. "Fibre optic sensor physiological parameters" *Electronics Letters*, Oct. 15, 1998, pp. 1991-1993.

\* cited by examiner

WAVEGUIDE AND OPTICAL MOTION SENSOR USING OPTICAL POWER MODULATION

CROSS-REFERENCE TO RELATED APPLICATIONS

This application claims the benefit of and priority to U.S. Provisional Patent Application Ser. No. 60/898,269, filed on Jan. 31, 2007 and U.S. Provisional Patent Application Ser. No. 60/998,745, filed on Oct. 15, 2007, titled "Method for Measurement of Physiological Pulses Using a Deformable Optical Waveguide," all of which are herein incorporated by reference in their entirety.

TECHNICAL FIELD

This invention relates to an optical motion sensing system using optical power modulation and a waveguide adapted for use in an motion sensing system.

BACKGROUND

Blood pressure refers to the force exerted by circulating blood on the walls of blood vessels and constitutes one of the principal vital signs. The systolic pressure is the peak pressure in the arteries, which occurs near the beginning of the cardiac cycle. The diastolic pressure is the lowest pressure, which is at the resting phase of the cardiac cycle. The average pressure throughout the cardiac cycle is reported as the mean arterial pressure. The pulse pressure reflects the difference between the maximum and minimum pressures measured.

Blood pressures can be measured invasively (by penetrating the skin and measuring inside the blood vessels) or non-invasively. The former is usually restricted to a hospital setting. The non-invasive auscultatory and oscillometric methods are simpler and quicker than invasive methods, have less complications, and are less unpleasant and less painful for the patient. Non-invasive measurement methods are more commonly used for routine examinations and monitoring.

The auscultatory method typically uses a stethoscope and a sphygmomanometer. An inflatable cuff is placed around the upper arm at roughly the same vertical height as the heart and pneumatically connected to a mercury manometer or aneroid gauge. The mercury manometer measures the height of a column of mercury, giving an absolute cuff pressure measurement without need for calibration and consequently not subject to the errors and drift of calibration which affect other pressure gauges. The cuff is inflated manually by repeatedly squeezing a rubber bulb until the brachial artery is completely occluded. While listening with the stethoscope over the brachial artery distal to the pressurized cuff, the examiner slowly releases the pressure in the cuff. When blood just starts to flow in the artery, the turbulent flow creates a "whooshing" or pounding sound (first Korotkoff sounds). The pressure at which this sound is first heard is the systolic blood pressure. The cuff pressure is further released until no sound can be heard (fifth Korotkoff sound), at the diastolic blood pressure.

Oscillometric methods are sometimes used for continuous monitoring and sometimes for making a single measurement. The equipment is functionally similar to that of the auscultatory method but does not rely on the use of a stethoscope and an examiner's ear. Instead, the detection means is a pressure sensor that is pneumatically connected to the cuff and registers the (relatively small) oscillations in cuff pressure that are synchronous with the arterial pressure waveform. The first oscillation in cuff pressure does not occur at the systolic pressure, but at a cuff pressure substantially above systolic pressure. The cuff is initially inflated to a pressure in excess of the systolic blood pressure. The cuff pressure is then gradually reduced. The values of systolic and diastolic pressure are calculated from the different oscillation amplitudes that occur at various cuff pressures by the use of an algorithm. Algorithms used to calculate systolic and diastolic pressure often use experimentally obtained coefficients aimed at matching the oscillometric results to results obtained by using the auscultatory method as well as possible.

SUMMARY

Accordingly, an optical motion sensor is described herein the uses optical power modulation. The optical motion sensor can be used in an improved vital sign (e.g., blood pressure) measurement device described below. The motion sensor device operates on the principle of optical power modulation, namely that downward displacement of a sensor pad can cause the flexing and/or compression of an optical waveguide to result in a reduction in an amount of optical energy transmitted to the second end of the optical waveguide with increased compression and/or flexing of the optical waveguide. By monitoring the amount of light that exits the second end of the optical waveguide, data regarding the amount of displacement can be obtained. The data regarding the amount of displacement can be used, for example, in a vital sign measurement device and used to determine various vital signs. An optical detector can be optically coupled to the optical waveguide such that the optical detector receives substantially all of the optical energy from the optical source that does not escape from the sides of the optical waveguide.

In some aspects, an optical motion sensing device can include a sensor frame defining an opening, a sensor pad disposed in the opening, an optical sensing system adapted to detect an amount of movement of the sensor pad in the sensor frame, and an output unit. The optical sensing system includes an optical waveguide, an optical source device, and an optical detector. The optical waveguide is positioned within the sensor frame such that the movement of the sensor pad results in the flexing or compressing of the optical waveguide. The optical source device supplies optical energy to the optical waveguide. The optical detector detects an amount of optical energy exiting the optical waveguide. The output unit is configured to receive a signal indicative of the amount of optical energy exiting the optical waveguide and to generate a measure of the amount of movement of the sensor pad from the received signal.

In some implementations, a maximum contact pressure applied to the sensor pad can cause a reduction of 20-80% (e.g., a 50-70% reduction) in the total amount of light exiting the optical waveguide. In some implementations, the device can include a load spring attached to at least a portion of the sensor frame and also supporting the sensor pad. The load spring can be configured to counter at least some of the pressure exerted against the sensor pad. The load spring can be adapted to allow a desirable displacement of the sensor pad at a maximum pressure. In some implementations, the load spring can be adapted to provide a maximum displacement of the sensor pad between 0.5 and 3 millimeters at a maximum pressure.

In some implementations, the device can include a waveguide support structure having a non-compliant surface to support at least a portion of the optical waveguide. The optical sensing system can be adapted to cause a flexural deformation in an unsupported portion of the optical waveguide in response to a displacement of the sensor pad.

In some implementations, the device can include a flexible and incompressible support surface that supports the optical waveguide over substantially all of its length. For example, the waveguide support surface can be a flexible electronic circuit board. The waveguide can be bonded to the support surface with a flexible elastomer adhesive. In some implementations, the optical source device and/or the optical detector can be mounted on the surface of the waveguide support surface. Furthermore, associated electronic components can also be mounted on the waveguide support surface. In some implementations, the waveguide support surface can include a support return element which is configured within the support surface and adapted to oppose the flexing of the support surface. In some implementations including a sensor pad, the support return element can be adapted to provide an increasing contact pressure between the sensor pad and the optical waveguide as the sensor pad moves from a rest position to a position of maximum displacement. The optical waveguide can be adapted such that said increasing contact pressure causes a decreasing amount of light exiting the second end of the optical waveguide.

In some aspects, a method of detecting an amount of localized displacement can include transmitting optical energy into a first end of the optical waveguide, detecting an amount of optical energy exiting a second end of the optical waveguide, and generating a measure of an amount of downward displacement of a sensor pad based on the amount of optical energy exiting the second end of the optical waveguide. The optical waveguide is positioned within a sensor frame including the sensor pad such that the downward displacement of the sensor pad results in the compression or flexing of the optical waveguide. The amount of optical energy exiting the optical waveguide is detected using an optical detector held by the sensor frame. The optical detector generates therefrom a signal indicative of optical energy received. The generated measure of the amount of downward displacement of the sensor pad is generated using the signal indicative of the optical energy exiting the second end of the optical waveguide. The amount of optical energy exiting the second end of the optical waveguide is reduced in response to the downward displacement of the sensor pad.

In some aspects, a compliant waveguide for detecting arterial pulses includes a cladding having a flat surface and defining a lumen and a core disposed within the lumen. The cladding includes an elastomer having a Shore A hardness of between 25 and 75. The core also includes an elastomer having a Shore A hardness of between 25 and 75. The core has a refractive index greater than the refractive index of the cladding.

In some implementations, the cladding can have a Shore A durometer of between 45 and 55 and the core can have a Shore A hardness between 30 and 45. In some implementations, the waveguide can be capable of guiding at least 10,000 modes (e.g., at least 50,000 modes). In some implementations, the core can have a refractive index between 1.43 and 1.50 (e.g., between 1.45 and 1.47) and the cladding can have a refractive index between 1.39 and 1.48 (e.g., between 1.39 and 1.41). In some implementations, the core can have a radius of at least 45 micrometers (e.g., between 150 and 200 micrometers).

In some implementations, the optical waveguide can include an elastomer (e.g., a siloxane elastomer). The elastomer can be selected from the group consisting of polysiloxane, polyurethane, polybutadine rubber, and combinations thereof.

The details of one or more implementations of the invention are set forth in the accompanying drawings and the description below. Other features, objects, and advantages of the invention will be apparent from the description, drawings, and claims.

DESCRIPTION OF DRAWINGS

Like reference symbols in the various drawings indicate like elements.

DETAILED DESCRIPTION

Figure 1:
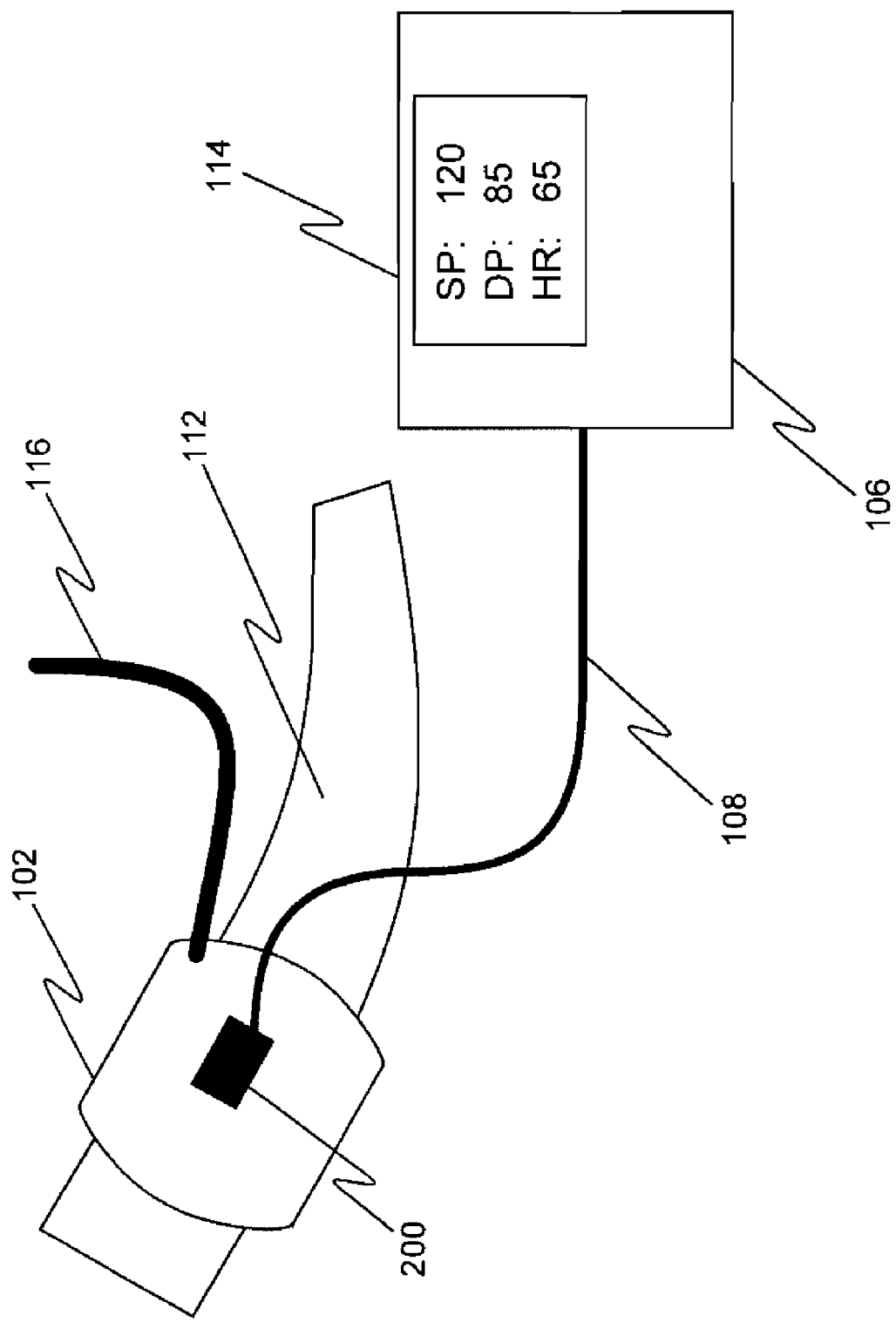
FIG. 1 depicts one implementation of the vital sign measurement device.

As shown in FIG. 1, a vital sign measurement device can include a sensor fixation device 102, a sensor frame 200 holding an optical sensing system, and an output unit 106. An output from the optical sensing system in the sensor frame 200 can be used to determine the measurement of a vital sign, for example, blood pressure of a patient, and specifically systolic and diastolic measures for the blood pressure of the patient.

The sensor fixation device 102 holds the sensor frame 200 and applies it against an anatomical location of a subject 112, within which is an artery 118. In the FIG. 1, for example, the anatomical location 112 is an upper arm of a human patient. The sensor frame 200 can be positioned so that the optical sensing system 104 senses movement corresponding to an arterial pulse when the sensor frame 200 is placed against the anatomical location 112 of the subject. In this manner it is possible to detect arterial pulses with the optical sensing system when the sensor fixation device 102 is exerting a pressure on the subject's arm 112 that is at or below systolic pressure, but not detect arterial pulses when the sensor fixation device 102 is above systolic pressure. Accordingly, systolic pressure can be determined as the pressure applied to the anatomical location 112 when the first arterial pulse is detected by the optical sensing system, as a pressure is reduced from a pressure exceeding systolic pressure. Alternatively, systolic pressure can be determined to be the last pressure at which an arterial pulse is observed by the optical sensing system, as the pressure is as the pressure is increased to a pressure exceeding systolic pressure. Furthermore, the vital sign measurement device can measure the relative strength of one or more arterial pulses, and/or detect a pulse waveform, when the sensor fixation device is exerting a pressure of less than systolic pressure on the patient's arm, and from those measurements, determine a number of different vital sign measurements including systolic and diastolic pressure measurements for the subject. For example, diastolic pressure can be determined based on predetermined pulse waveform characteristics, such as a ratio of pulse amplitudes and/or the shape of the pulse waveform between arterial pulses.

The optical sensing system 104 employs what may be referred to as an optical power modulation method to detect and measure arterial pulses. An example optical sensing system that implements such an optical power modulation method, referring in particular to FIG. 5C, includes an optical waveguide 212 held by the sensor frame 200, an optical source 202 positioned to supply optical energy to a first end of the optical waveguide 212, and an optical detector 240 positioned to detect an amount of optical energy exiting a second, opposite end of the optical waveguide 212. An output unit 106, for example as shown in FIG. 1, is connected so as to receive a signal, for example an electrical signal, from the optical sensing system, and in particular from the optical detector 240, wherein the signal is indicative of an amount of light at a given point in time exiting the second, opposite end of the optical waveguide that is detected by the optical detector 240. From that received signal, the output unit 106 generates a measure of the vital sign. The optical sensing system 104 is acted upon, or responds to, an arterial pulse by virtue of the compression or flexing of at least one portion of the optical waveguide 212 of the sensing system, which results in a reduction to the amount of optical energy exiting the optical waveguide and accordingly a reduction in the amount of optical energy received by the optical detector.

By way of example, a vital sign can include a heart rate, an arterial pulse waveform, a systolic blood pressure measure, a diastolic blood pressure measure, a mean arterial blood pressure measure, a pulse pressure measure, and/or a measurement of arterial compliance. In some implementations, the vital signs can be determined from the timing of arterial pulses, the amplitude and/or magnitude of arterial pulses, and/or from arterial pulse waveforms. In some implementations, the vital signs can be determined from output received from the optical sensing system 104 alone, while in other implementations the vital signs can be determined from that output in combination with other data (e.g., data regarding the pressure within a pneumatic cuff). As example of the former case, a heart rate can be determined from the output received from the optical sensing system 104 alone. The present vital sign measurements can be taken in any limb location, including but not limited to the upper arm, the wrist area, the legs, and the digits.

Sensor Fixation Device

The sensor fixation device can be any structure adapted to hold and position a sensor frame 200 or a portion thereof adjacent to an anatomical location of a subject 112 such that the optical sensing system 104 within the sensor frame 200 can detect an arterial pulse. The sensor fixation device can hold the sensor frame 200 adjacent to an anatomical location of a subject 112 at a predetermined sensor fixation pressure or at an adjustable sensor fixation pressure. For example, the sensor fixation device can be an adhesive bandage or a cuff (e.g., an elastic cuff or an inflatable cuff).

Figure 4:
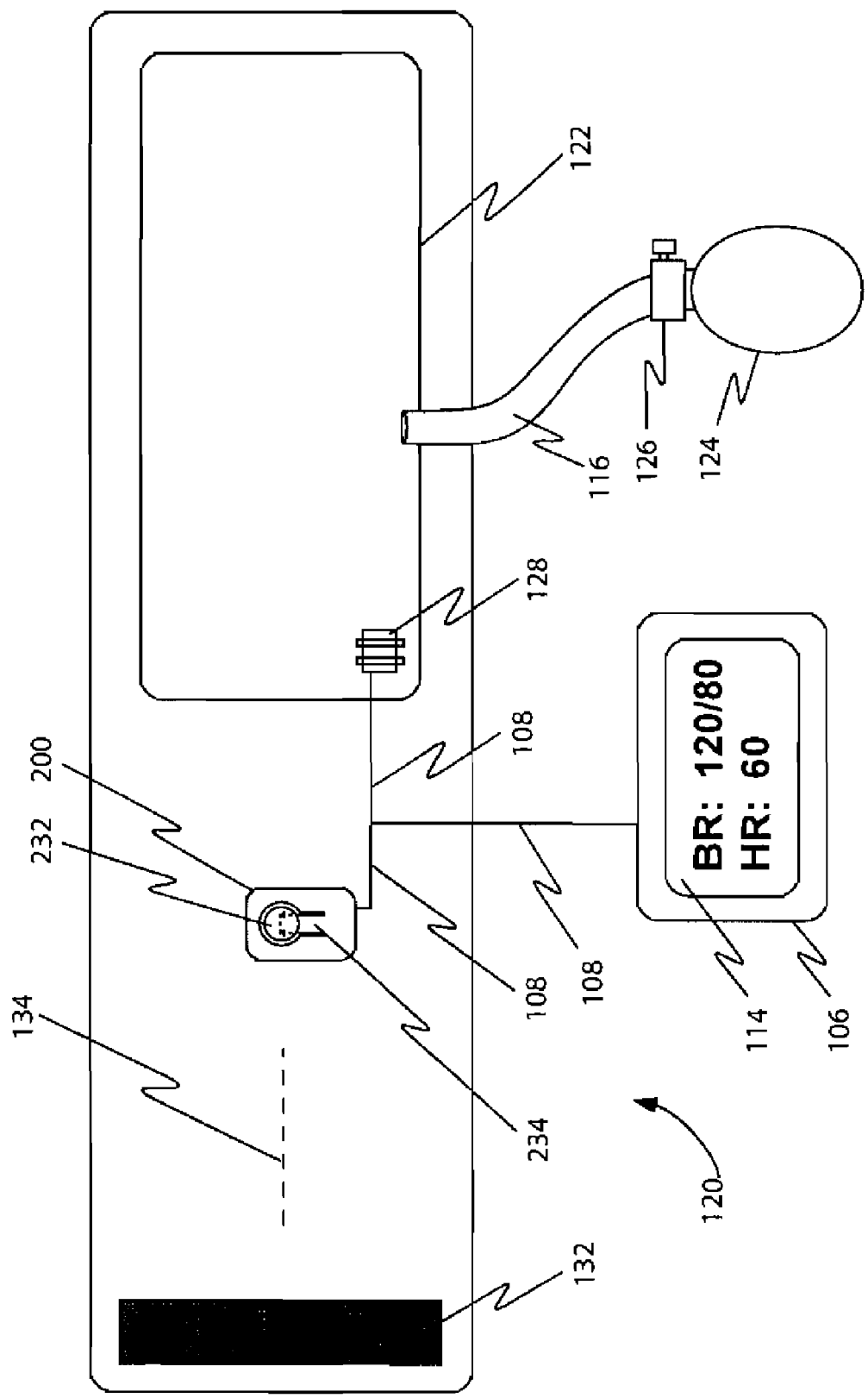
FIG. 4 depicts an implementation of a vital sign measurement device having a sensor fixation device with an inflatable bladder.

As shown in FIG. 4, a sensor fixation device 102 can be an inflatable cuff 120 having an inflatable bladder 122. For example, the sensor fixation device 102 can be an assembly that includes a cuff comprising a fabric material that is configured to surround or encircle an anatomical location (e.g., a limb) of a subject. The inflatable bladder 122 can be positioned within the cuff to partially surround or encircle a limb. As such, the sensor fixation device 102 is adapted to apply pressure to the limb when inflated and thereby compress an artery within the limb.

Figure 12:
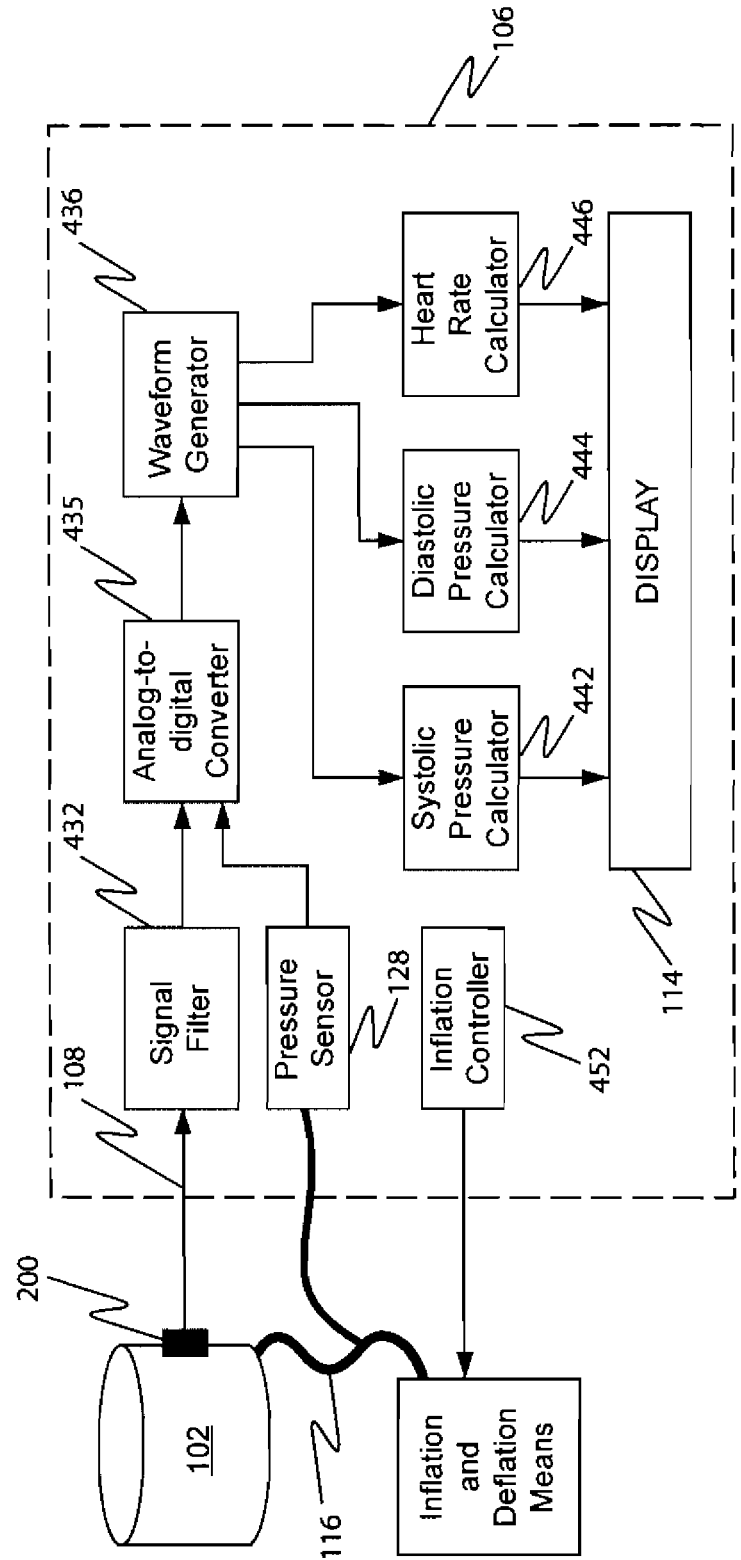
FIG. 12 depicts an implementation of an analytical method used to determine one or more vital signs by the output unit.

Generally, a cuff-type sensor fixation device 102 for use in the presently described systems and methods can be of a type that either completely or partially encircles the limb, or may be of a type that applies pressure locally as may be advantageous in certain anatomical locations, including the wrist over the radial artery. The bladder 122 in such a device 102 can be pneumatically connected to a pump 124 via a hose 116, as is the case in FIG. 4. In some implementations such as that shown in FIG. 4, a pneumatically inflatable cuff can be inflated (e.g., via a pump 124) and deflated (e.g., via a valve 126) to adjust the pressure applied to a portion of a subject's body 112. In some implementations, a system can include an inflation controller 452, such as is included in the output unit 106 as shown in FIG. 12, to control the inflation and deflation of the cuff. In other implementations, an inflation controller can be included as a separate controller unit to control the operation of the vital sign measurement device.

As such, various forms of a sensor fixation device can be applied to various different portions of a subject's body. The sensor fixation device can be sized and arranged for placement at an anatomical location of a subject's body adjacent to a predetermined artery of the subject. As shown in FIGS. 1 and 2A-2C, the sensor fixation device 102 can be positioned on an upper arm (above a subject's elbow) so that the optical sensing system within the sensor frame 200 can sense movement corresponding to an arterial pulse in the brachial artery 118. The sensor fixation device can also be adapted for placement on the wrist so that the optical sensing system in the sensor frame can sense movement corresponding to an arterial pulse in the radial artery. The sensor fixation device can also be positioned on a leg (e.g., at the ankle to detect pulses in an artery), the neck, or any other part of the body where an arterial pulse can be detected.

Figure 2A:
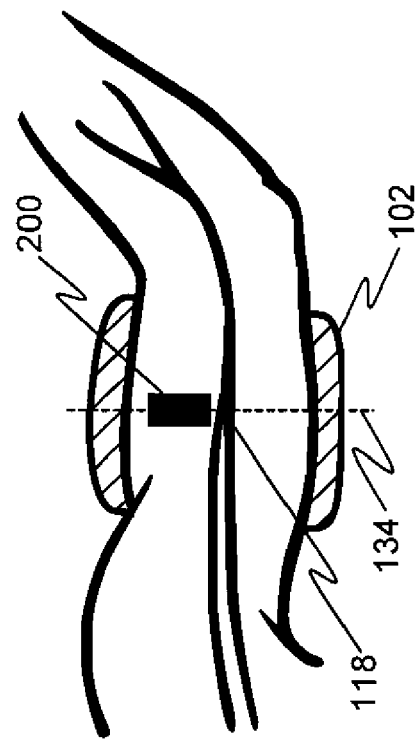
FIGS. 2A, 2B, and 2C depict various implementations of the vital sign measurement device positioned on an upper arm, and showing three different levels of cuff pressure relative to arterial systolic pressure.
Figure 2B:
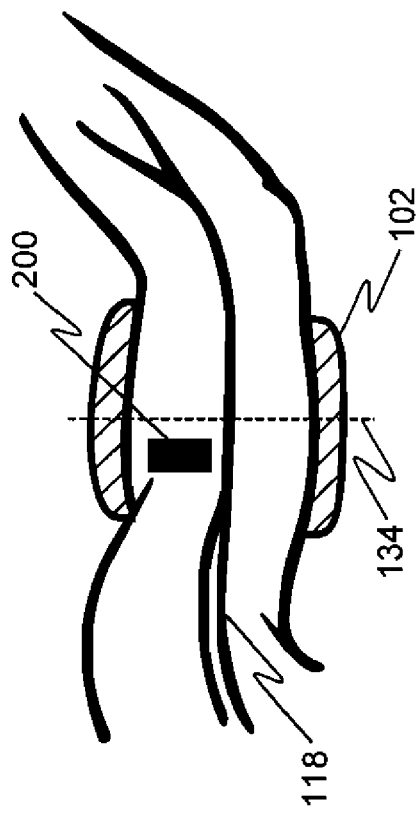
Figure 2C:
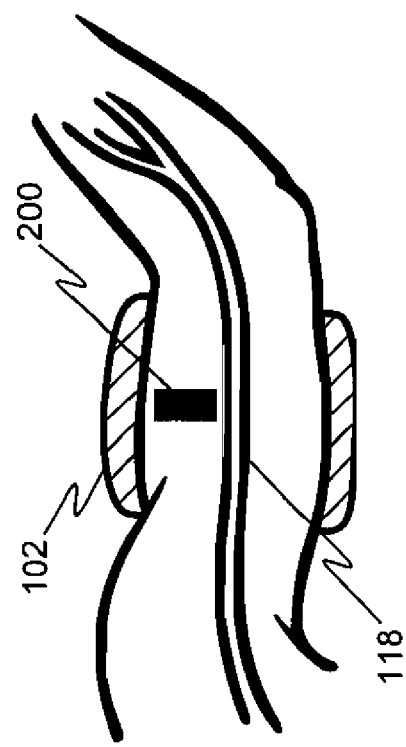

As shown in FIGS. 2A-2C, the sensor frame 200 can be positioned proximal to the midpoint of the sensor fixation device 102 (as shown in FIG. 2A), at the mid point of the sensor fixation device 102 (as shown in FIGS. 2B and 2C), or distal to the mid point of the sensor fixation device 102 (not shown). The placement of the sensor frame 200, and more specifically the sensing portion (e.g., a sensor pad) of the sensor frame 200, with respect to a pressure imparting device can impact the data obtained. In implementations where the sensor fixation device 102 applies pressure to the anatomical location, such as shown in FIGS. 2A-2C, the position of the sensing portion of the sensing frame 200 within the sensor fixation device 102 can impact the data obtained. In some implementations, a pressure applied to an artery lying below the surface of an anatomical location can be non-uniform. For example, although a pressure imparting body placement device 102 can apply a uniform pressure, the pressure transmitted through the layers of tissue can result in a non-uniform pressure against an artery lying some distance below the surface. In some implementations, the pressure applied to an artery lying some distance below the skin by an inflatable cuff can be greatest at the cuff midline and less at the cuff margins. The location of the sensor frame 200 relative to the sensor fixation device 102 can be fixed to optimize the sensitivity to selected features of the arterial pulse. In some implementations, the sensor frame 200 and the sensing portion (e.g., the sensor pad) of the sensor frame 200 can be located at the midline 134 of the cuff such that it is not responsive to pulsatile enlargement of the arterial segment under the proximal part of the cuff when the cuff pressure exceeds systolic pressure, thereby allowing a precise determination of the systolic pressure when the midsection of the arterial segment opens.

In other implementations, not shown, the sensor frame 200 and the sensing portion (e.g., a sensor pad) of the sensor frame 200 can be located near the distal margin of the cuff such that it is responsive specifically to the pulsatile arterial dimension changes at that location. Accordingly, the unique features of the arterial pulse waveform at diastolic pressure at a distal position can be identified, and effects of arterial compliance in more distal arteries can be detected. Outward flexing of the skin at the midline 134 of the cuff, and also distal to the midline 134, occurs during systole when the cuff pressure is below systolic pressure. At cuff pressures exceeding systolic blood pressure, the arterial oscillations are limited to the proximal area of the cuff, as discussed above.

In some implementations, not shown, the device can include a second pressure imparting device separate from the sensor fixation device holding the sensor frame having the optical sensing system. The second pressure imparting device can be adapted to be placed against a second anatomical location of a subject proximal to the anatomical location of the sensor fixation device to allow for arterial pulse detection by the optical sensing system at a position distal to and separated from the pressure imparting device. Accordingly, the optical sensing system can detect an arterial pulse waveform at a position spaced away and distal to the point of arterial occlusion, and thus allow for the detection of unique features of an arterial waveform. The second pressure imparting device can be an inflatable cuff. In some implementations, both the pressure imparting device and the sensor fixation device can be inflatable cuffs.

FIG. 2A depicts a sensor fixation device 102 imparting a pressure on the arm exceeding arterial systolic pressure of the brachial artery sufficient to result in a minimal arterial opening under the leading edge of the sensor fixation device 102 at systole. The amount of pressure imparted against the sensor fixation device 102 will pulsate slightly due to the arterial expansion at the leading edge during an arterial pulse. No arterial opening occurs at the positioning of the sensor frame 200, and therefore the optical sensing system 104 in the sensor frame 200 does not produce a pulsatile signal. A pulsatile signal, however, will occur at a higher pressure if the sensor frame 200 is located at a position proximal to the midpoint of the sensor fixation device 102 than if it is located at the midpoint of the sensor fixation device 102.

FIG. 2B depicts a sensor fixation device 102 imparting a pressure slightly exceeding arterial systolic pressure, such that the arterial opening 118 extends nearly to the midpoint of the sensor fixation device 102 at systole. The oscillation in pressure imparted against the sensor fixation device 102 during an arterial pulse pressure would be much larger than in the case of FIG. 2A, as the arterial expansion occurs over nearly half of the segment located within the sensor fixation device. Nevertheless, no arterial opening occurs at the sensor fixation device 102 midpoint, and therefore the optical sensing system 104 in the sensor frame 200 does not produce a pulsatile signal.

FIG. 2C depicts a sensor fixation device 102 imparting a pressure below arterial systolic pressure, such that the entire artery segment 118 opens momentarily at systole. The oscillations in pressure imparted against the sensor fixation device 102 during an arterial pulse will be even greater in amplitude. The arterial opening at the location under the sensor frame 200 causes the optical sensing system 104 to register a pulsatile signal.

Figure 3:
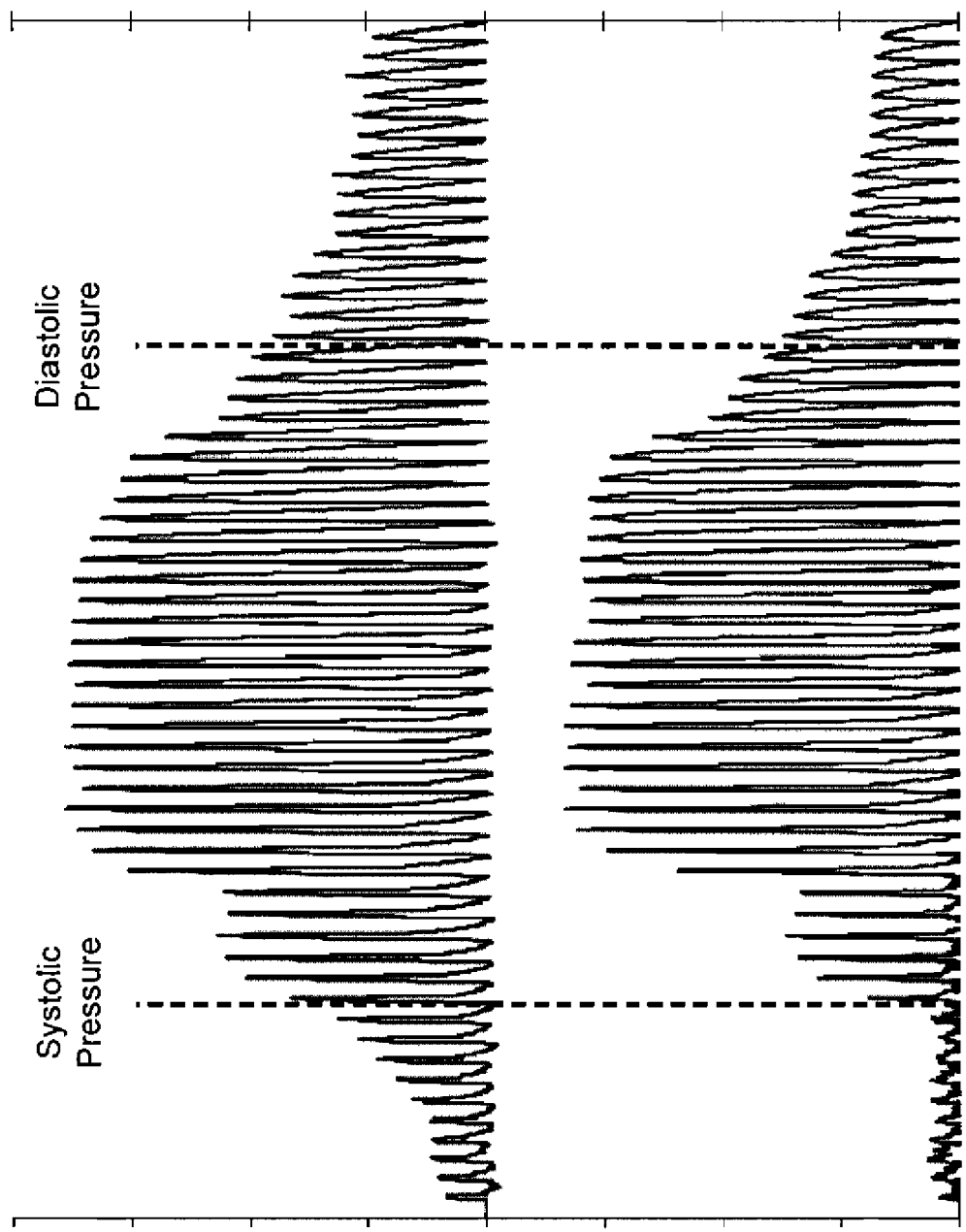
FIG. 3 depicts a series of pulses during deflation of a cuff detected by a pressure sensor pneumatically coupled to the cuff compared to simultaneously obtained pulses detected by an optical sensing system held by a sensor fixation device.

The top portion of FIG. 3 depicts pressure pulses sensed in a sensor fixation device 102 imparted by the series of arterial pulses as the imparted pressure by the sensor fixation device 102 is decreased from a pressure exceeding systolic blood pressure of a subject to a pressure below diastolic blood pressure of a subject. The bottom portion of FIG. 3 depicts pulses determined from the optical sensing system with the sensor frame at the midpoint of a sensor fixation device 102 as the pressure imparted by the sensor fixation device is decreased from a pressure exceeding systolic blood pressure of a subject to a pressure below diastolic blood pressure of a subject. As shown, the optical sensing system within the sensor frame does not detect any pulses until the imparted pressure is at or below systolic blood pressure. This can allow for an accurate determination of systolic blood pressure and the waveform detected by the optical sensing system can allow for the calculation of other vital signs.

FIG. 4 depicts one implementation of a sensor fixation device 102. The sensor fixation device can be an inflatable cuff 120 having an inflatable bladder 122. The cuff can include a fabric material configured to surround a limb of a subject. The inflatable bladder 122 can partially, but not completely, encircle the limb, and can be adapted to apply pressure to the limb when inflated and thereby compress an artery within the limb. The inflatable cuff 120 can be adapted to be wrapped around the upper arm of a subject and to hold a sensor frame 200 in a position to apply equal pressure to the limb. An optical sensing system can be located within the sensor frame 200 to detect arterial pulses from the brachial artery. The cuff 120 can include hook and loop fasteners 132 (e.g., Velcro®) or other fastening devices, which can be used to secure the cuff 120 around a limb of a subject. The cuff 120 can be wrapped around a subject's limb and the bladder 122 can be inflated to impart a pressure on the limb. The bladder 122 can be connected to a pump 124 by a hose 116. The bladder 122 can also be attached to a valve 126 which can control the deflation of the bladder 122. The pressure in the bladder 122 can be measured with a pressure transducer 128. The pressure transducer 128 can be located in the bladder, as shown, or can be pneumatically connected to the bladder 122 (e.g., via the hose 116).

The components of the optical sensing system can be packaged within the sensor frame 200 (e.g, a housing) located at the midpoint 134 of the cuff 120. The sensor frame 200 can be attached to the cuff at a location that is not coincident with part of the bladder. The sensor frame 200 can be in opposition on the cuff such that the pressure applied to the limb by the sensor frame is substantially equal to the pressure applied to the limb by the surrounding cuff fabric when the inflatable bladder 122 is inflated. For example, the upper surface of the sensor frame 200 can be approximately flush with an inside surface of the cuff. The sensor frame 200 can be positioned on the cuff 120 so that the optical sensing system 104 can sense a pulse of an artery when the cuff 120 is wrapped around an anatomical location of a patient.

Output Unit

As shown in FIGS. 4 and 12, the output unit receives signals (e.g., electrical signals) representative of an amount of optical energy (e.g., light) exiting the second end of the optical waveguide and thus detected by the optical detector 240. These signals can be transmitted via electrical wires 108. In some implementations, the output unit 106 can also receive other data. For example, as shown in FIG. 4, wires 108 can transmit data in the form of signals (e.g., electrical signals) from a pressure transducer in the bladder 122 of a cuff 120 to the output unit 106 to allow the output unit 106 to determine an amount of pressure applied to an anatomical location of a patient. In some implementations, the output unit 106 can receive data regarding the amount of optical energy received by an optical detector from the optical sensing system via wireless transmission.

As shown in FIGS. 1, 4, and 12, the vital sign measurement device can include a display unit 114 to depict one or more vital signs (e.g., heart rate, systolic pressure, and diastolic pressure). As shown in FIG. 4, the output unit 106 can be packaged with the display unit 114. In some implementations, not shown, the output unit can be within the sensor frame, can be in another portion of the cuff assembly, or can be remotely located and in communication with the optical sensing system via wireless transmissions. Wires can transmit data (e.g., via electrical signals) from the output unit 106 to the display device 114. In other implementations, the output unit 106 can transmit vital sign measurements via wireless transmission.

In some implementations, the output unit can include an alarm system to produce a human detectable signal when a vital sign measurement generated by the output unit meets a predetermined criteria. For example, the output unit can be adapted to create a visual or audio alarm to alert a user that a detected vital sign is outside of a predetermined range.

The output unit 106 can perform a number of data processing steps, calculations, or estimating functions, some of which are discussed below. The output unit 106 can include a processor to determine the vital sign from signals from the optical sensing system with or without other data (e.g., data regarding a pressure applied to an anatomical location by an inflatable cuff as shown in FIG. 4).

Sensor Frame

Figure 5A:
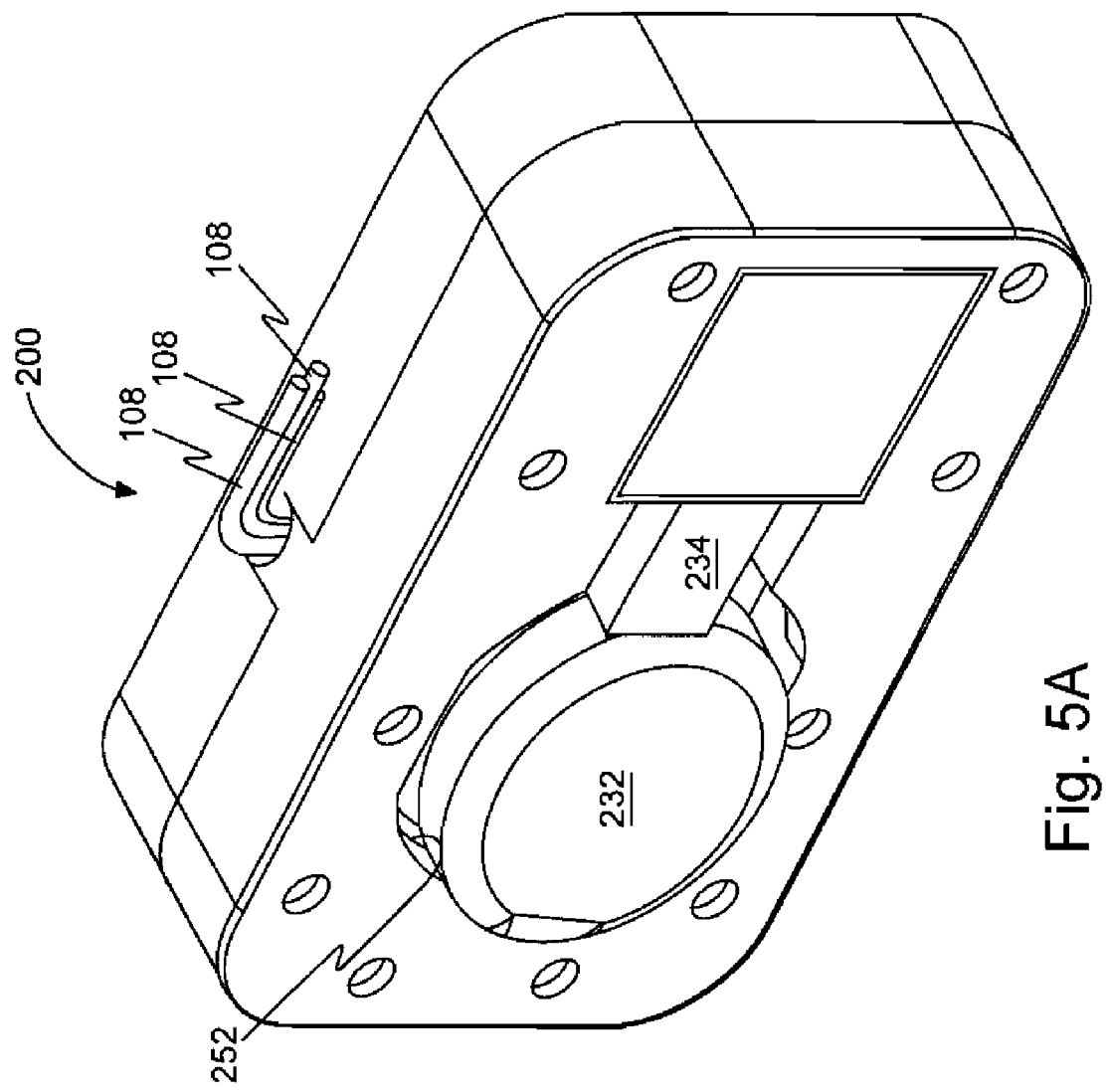
FIGS. 5A, 5B, and 5C depict an implementation of an sensor frame containing the components of an optical sensing system.
Figure 5B:
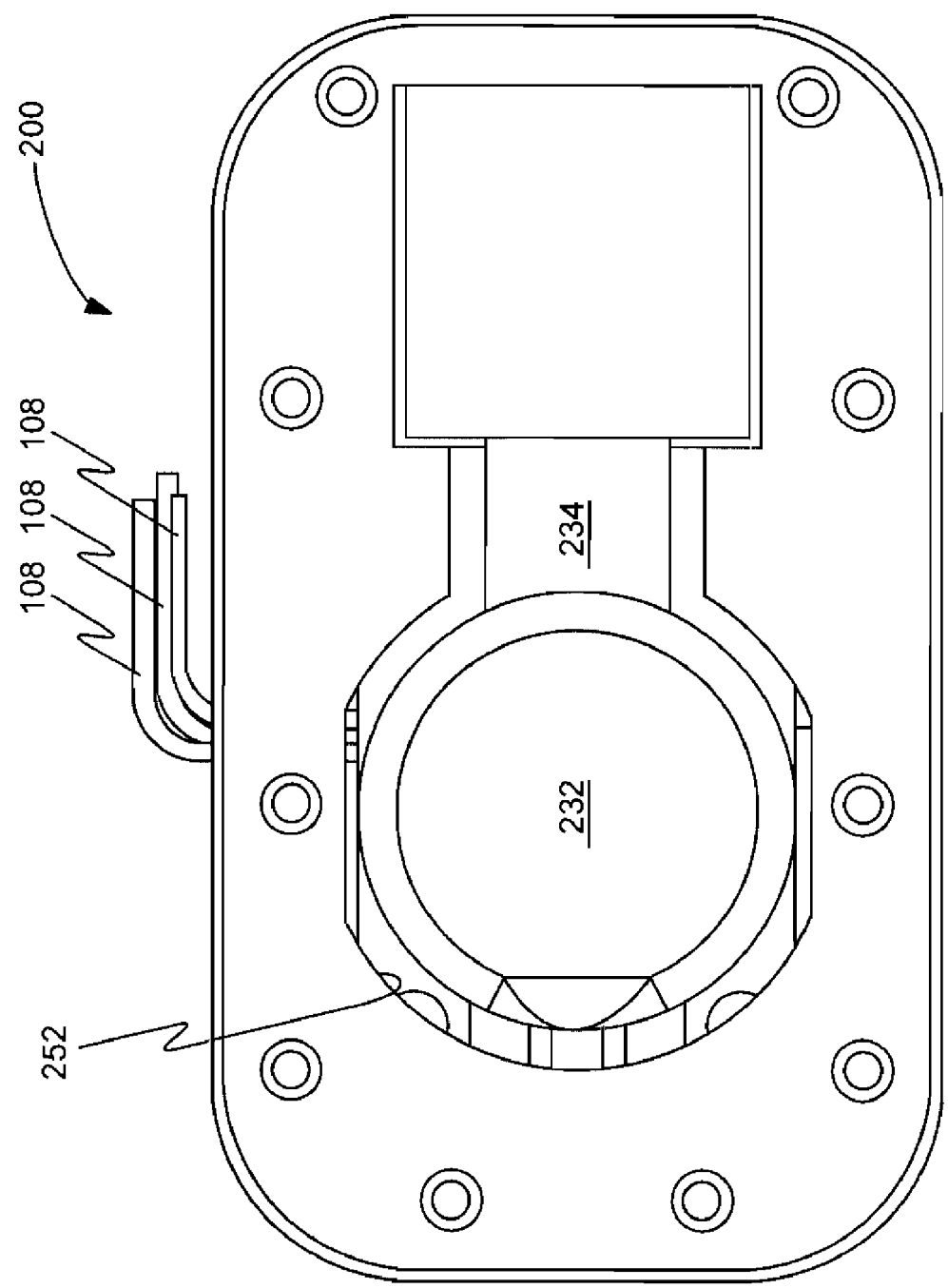
Figure 5C:
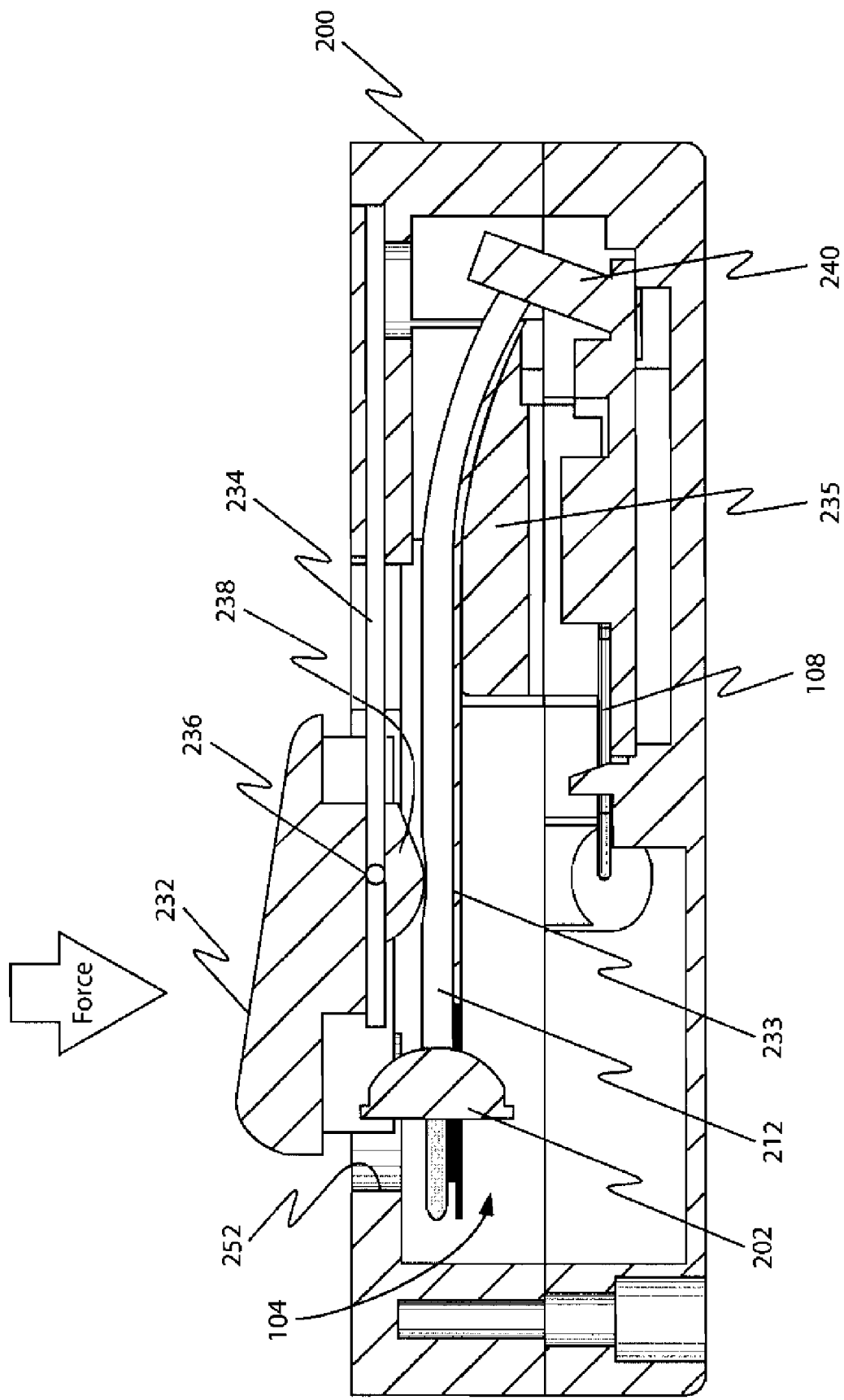

As shown in FIGS. 5A, 5B, and 5C, an optical sensing system 104 can be contained within a sensing frame 200 (e.g., a housing). The function of the sensor frame 200 is to maintain pressure against the skin and transmit the mechanical impulse of arterial pulses to the optical sensing system 104 without transmitting the pneumatic cuff pressure pulse. The function of the optical sensing system 104 is to generate a signal representative of the arterial pulse.

The sensor frame 200 can be placed against an anatomical location (e.g., against a subject's skin) to sense arterial pulses by the movement of the sensor pad 232, which can be positionable adjacent to the anatomical location. The sensor pad 232 can be configured such that it moves as a result of increased contact pressure caused by the inflation of the bladder. The movement of the sensor pad 232 can result in the compression or flexing of the optical waveguide 212. The sensor frame 200 can also include a load spring 234 attached to the sensor pad 232 to counter the force applied to the sensor pad 232 by the anatomical location of the subject. The load spring 234 can also be attached to at least a portion of the sensor frame 200. The sensor frame 200 can also include structures to support the waveguide, such as a flexible and incompressible waveguide support surface 233, upon which the waveguide rests, and/or a non-compliant waveguide support structure 235 to support the optical waveguide 212 against the forces applied to the optical waveguide 212 by the sensor pad 232. The sensor frame 200 can also include wires 108 to transmit data from the optical detector 240 to the output unit 106. In some implementations, not shown, the sensor frame 200 can include an output unit and can include wires that transmit data from the output unit to an external source (e.g., a display). In some implementations, the sensor frame 200 can have a width of between 0.7 and 1.3 inches (e.g., about 1 inch), a length of between 1.5 and 2.2 inches (e.g., about 1.7 inches), and a thickness of between 0.3 and 0.9 inches (e.g., about 0.6 inches).

As shown in FIGS. 5A, 5B, and 5C, a sensor pad 232 adapted for placement against an anatomical location of a subject can be attached to a load spring 234. The sensor pad 232 can extend out of the sensor frame 200 when in a relaxed state. For example, the sensor pad 232 can extend out of the sensor frame 200 by at least 0.1 inch (e.g., between 0.1 and 0.3 inches). As shown, the sensor pad 232 extends out from the sensor housing 200 by 0.161 inches. The sensor pad 232 can have any shape. The sensor pad 232 can have a diameter of at least 0.3 inches, for example between 0.3 and 0.8 inches (e.g., about 0.6 inches). In some implementations, for example as shown in FIG. 5C, the sensor pad 232 can be attached to the spring 234 by a hinge 236 that allows for the back and forth motion of the sensor pad 232. In some implementations, as shown in FIG. 5C, the sensor pad 232 can have an inclined upper surface. The sensor pad 232 can be attached to or otherwise positioned to cause the compression or flexing of the optical waveguide 212 of the optical sensing system 104. As shown in FIG. 5C, the sensor pad 232 can include a pressing portion 238 adapted to cause the localized compression of the optical waveguide 212. The sensor pad 232 can also be positioned within a cutout 252. The spacing between the cutout 252 and the sensor pad 232 can impact the amount of movement of the sensor pad 232 allowed by the sensor housing 200 due to arterial pulses. The spacing between the cutout 252 and the sensor pad 232 can be about 0.1 inches.

Wires 108 can transmit data from the optical detector 240 to an output unit 106, as discussed above. In some implementations, not shown, the output unit can be included within the sensor frame and wires can transmit vital sign data to devices outside of the housing. In some implementations, not shown, the optical sensing system 104 can transmit data from the sensor frame 200 by wireless transmission.

The load spring 234 can counter a force applied to the sensor pad 232 from an arterial pulse and return the sensor pad to an initial state after the arterial pulse. The load spring 234 can thus limit the amount of compression and flexural deformation of the waveguide due to an arterial pulse. The load spring 234 can be selected such that the optical transmission factor is most sensitive to waveguide deformation within the useful range of cuff pressures. The combination of the load spring 234 and other features of the sensor frame 200 and the optical sensing system 104 can provide countering forces such that an applied pressure of 150 mmHg will displace the sensor pad by at least 1 mm from a resting state. In some implementations, the sensor frame 200 and optical sensing system 104 can be adapted such that an applied pressure of 150 mmHg will displace the sensor pad by at least 2 mm from the resting state. In some implementations, the load spring 234 can be adapted to provide a maximum displacement of the sensor pad between 0.5 and 3 millimeters at a maximum pressure (e.g., between 0.8 and 1.5 millimeters at a maximum pressure). In some implementations, the sensor frame 200 and optical sensing system 104 can be adapted such that an applied pressure of between 80 and 150 mmHg (e.g., between 100 and 130 mmHg) can render an upper surface of the sensor pad approximately flush with an upper surface of the sensor frame 200. In some implementations, the sensor pad 232 can be nearly flush with the sensor frame 200 when placed against the anatomical location of a patient by the occluding device 102 with the occluding device providing a pressure to the anatomical location exceeding systolic pressure. In some implementations, the upper surface of the sensor frame 200 can be approximately flush with an inner surface of the sensor fixation device (e.g., the inflatable cuff).

Figure 6:
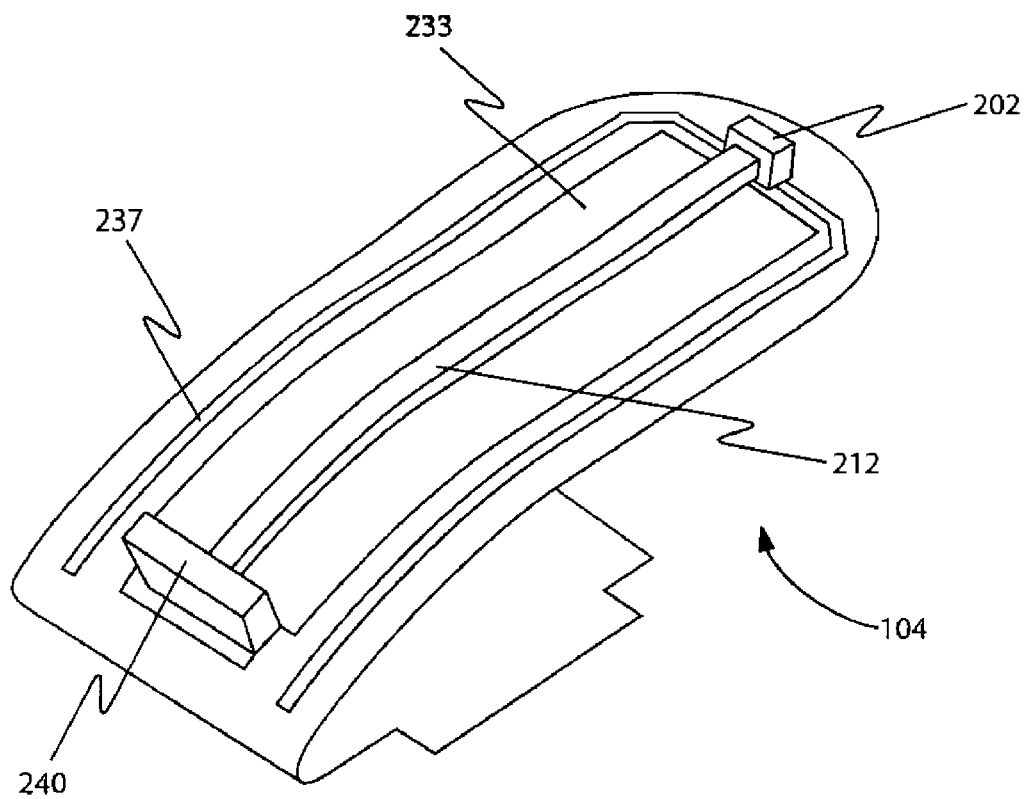
FIG. 6 depicts an implementation of the optical sensing system on a flexible an incompressible waveguide support surface.

The sensor frame 200 can also include a waveguide supporting structures, such as the flexible and incompressible waveguide support surface 233 and/or a non-compliant waveguide support structure 235 to support the waveguide 212 of the optical sensing system 104 against the force applied by the sensor pad 232. The waveguide support surface 233 can have a flexible and incompressible support surface and can extend along the entire length of the optical waveguide 212. In some implementations, as shown in FIG. 6, the waveguide support 233 can have a support return element 237 configured within the support surface and adapted to oppose the flexing of the support surface. For example, the support return element 237 within the waveguide support 233 can be a member with a high memory, such as a steel spring, which can return the waveguide to its non-deformed position following each pulsatile deformation. The support return element 237 can be adapted to provide an increasing contact pressure between the sensor pad and the optical waveguide as the sensor pad moves from a rest position to a position of maximum displacement, with the optical waveguide adapted such that said increasing contact pressure causes a decreasing amount of light exiting the optical waveguide. In some implementations, the support return element 237 can work with the load spring 234 to accomplish the increasing contact pressure. In some implementations, the waveguide support surface 233 can be a flexible electronic circuit board, to which the waveguide is bonded with a flexible elastomer adhesive. As shown in FIG. 6, the waveguide support surface 233 can also support and carry the optical source 202 and/or the optical detector 240. In some implementations, other associated electronic components can be mounted on the waveguide support surface 233.

Figure 7A:
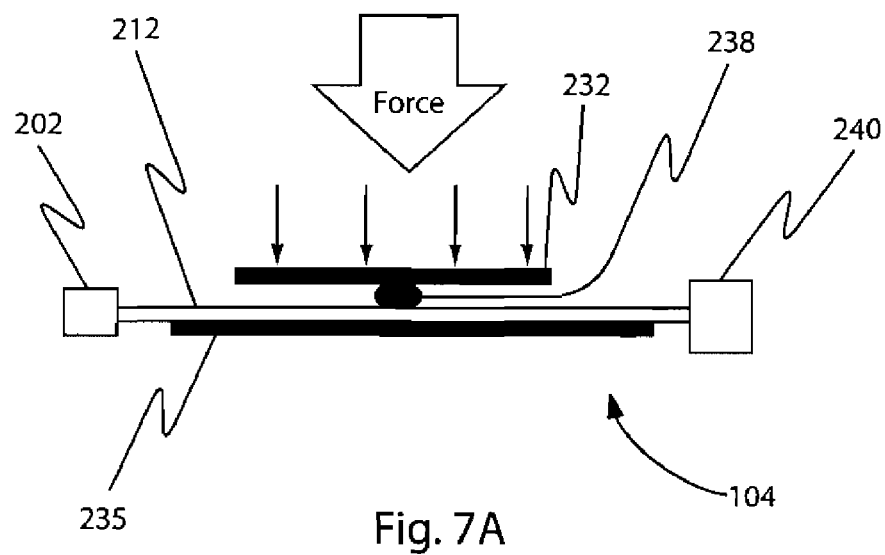
FIGS. 7A-7C depict implementations of optical sensing systems.
Figure 7B:
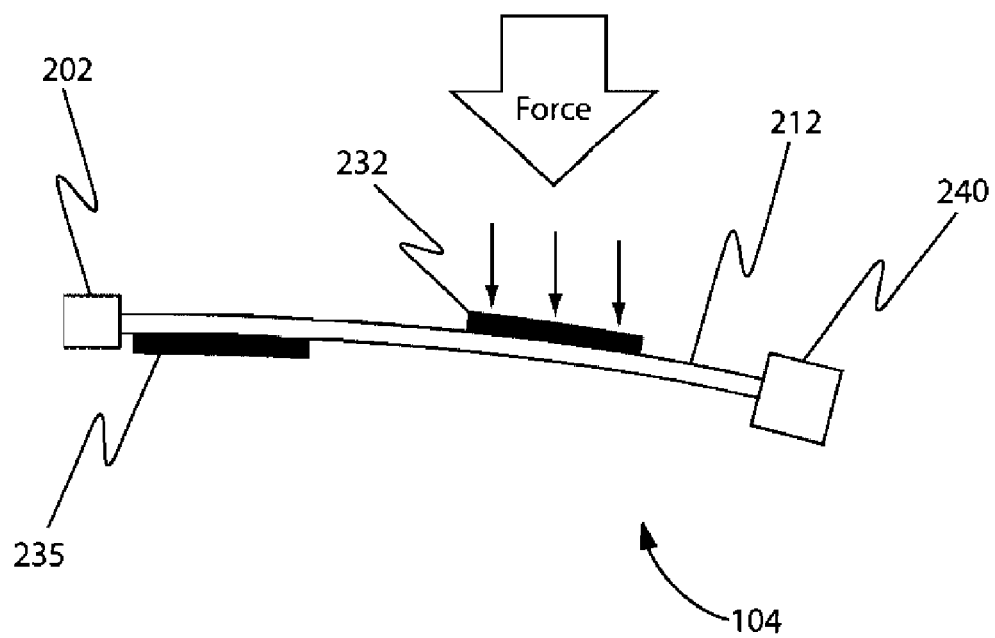
Figure 7C:
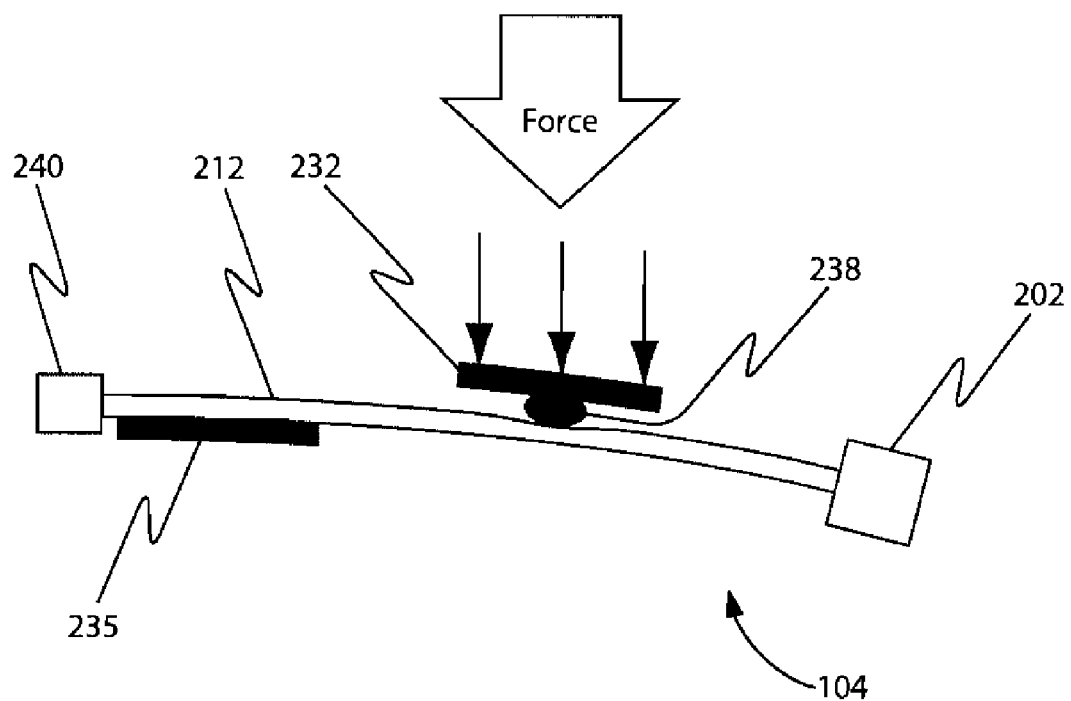

The waveguide support structure 235 is non-compliant. In some implementations, as shown in FIG. 7A the waveguide support structure 235 can support the portion of the waveguide 212 being acted upon by the sensor pad 232 (e.g., over substantially all of its length). Accordingly, the waveguide 212 can be compressed between the waveguide support 235 and pressing portion 238. FIGS. 5A and 8B, discussed below, depict how the compression of the waveguide 212 can result in a reduction in the amount of light transmitted to the optical detector 240. In other implementations, as shown in FIGS. 7B and 7C, the waveguide support structure 235 can support a portion of the waveguide spaced from the portion of the waveguide being acted upon by the sensor pad 232. In some implementations, the movement of the sensor pad 232 can result in the flexing of the waveguide 212. FIG. 7B depicts an implementation where the sensing pad acts directly against the waveguide to result in a flexing of the optical waveguide 212. FIG. 7C depicts an implementation where a pressing portion 238 presses against a localized portion of the waveguide. This can result in some compression combined with some flexing of the waveguide in an adjacent region. FIGS. 9A, and 9B, discussed below, depict how the flexing of the waveguide 212 can result in a reduction in the amount of light transmitted to the optical detector 240.

The optical sensing system 104 within the sensor frame 200 can act as a motion sensing system (e.g., a motion sensing system adapted to detect localized motion associated with an arterial pulse). The optical sensing system 104 within the sensor frame 200 can detect motion corresponding to an arterial pulse when the sensor fixation device is placed against the anatomical location of the subject, rather than merely a pressure applied to the sensor pad 232. For example, a surface pressure sensor (e.g., a piezoresistive type pressure sensor) can detect changes in pressure due to an arterial pulse even when the pressure applied to the anatomical location by the occluding device 102 exceeds systolic pressure. At high cuff pressure (above systolic pressure) the artery proximal to the occluding device 102 (e.g., an inflatable cuff) can impart a pulsatile impact to the anatomical location delivered through the tissue, which causes a pulsatile pressure increase within the occluding device 102. This effect causes a pulsatile tensioning of the occluding device 102, which would be detected by a surface pressure sensor attached to the inside surface of the occluding device 102, even though there is no cuff contraction because the tissue is essentially "incompressible" and the artery is continuously occluded in the area underneath the pressure sensor. A signal of an amount of pressure applied by the occluding device (i.e., a cuff bladder pressure sensor) and the surface pressure sensor will be similar above and below systolic pressure because the effect of the opening of the artery to allow blood flow to occur is smaller than the effect of the pulsatile impact to the cuff described above. In contrast, an optical sensing system within a sensor frame acting as a motion sensor can have little to no response due to the tensioning of the cuff at high cuff pressures and prevent the detection of motion during arterial pulses at pressures above systolic pressure. Accordingly, the use of an optical sensing system within a sensor frame as a motion sensor can more accurately indicate the systolic blood pressure than a pressure sensor. Furthermore, no separate accurate blood pressure measurement is needed for calibration or establishment of a baseline.

Optical Sensing System Using Optical Power Modulation

As shown in FIGS. 5C, 6, and 7A-7C, the optical sensing system 104 can include an optical source 202, an optical waveguide 212 and an optical detector 240. As discussed above, the optical sensing system 104 can be held by a sensor frame 200 (e.g., a housing) held by the sensor fixation device 102. The optical source 202 can be optically coupled to the optical waveguide 212, such that the optical energy (e.g., light waves 218) travels from the optical source 202 into a first end of the optical waveguide 212. In some implementations, an LED can be used as the optical source 202. An optical detector 240 receives the optical energy exiting an opposite, second end of the optical waveguide 212 and can generate a signal indicative of the amount of light received. In some implementations, the optical detector 240 receives substantially all of the light exiting the second end of the optical waveguide 212. In some implementations, the optical detector 240 can be a PIN diode photodetector, a CCD (Charge-Coupled Device) detector, or a CMOS (Complementary Metal-Oxide-Semiconductor) detector.

Optical Waveguide

The optical waveguide 212 can be an optical fiber or any liquid, gel, or solid that transmits light waves by internal reflection or refraction. An optical waveguide 212 can include a length of optically clear material, commonly referred to as the "core" 215, which is surrounded by a material of lower refractive index, commonly referred to as the "cladding" 217. The core 215 can have a relatively high index of refraction ($N_2$), with respect to the lower index of refraction ($N_1$) of the cladding 217. The difference between the core and cladding refractive indices defines the numerical aperture (NA) of the waveguide, according to the relationship:

$$NA=(N_2^2-N_1^2)^{1/2}$$

It is the NA and the critical angle ($\theta_c$) of a waveguide that govern the confinement of light within the core of the waveguide. If the incidence angle of a light ray at the core/cladding interface with respect to a normal vector to the interface is less than the critical angle ($\theta_c$), then the ray will not be internally reflected but will escape the core and be lost. If $N_2$ is very close to $N_1$ (i.e., NA→0), the critical angle will approach 90 degrees and nearly all the light will escape within a short length of waveguide. If $N_2$ and $N_1$ are sufficiently different in value, a large portion of the light will remain confined. Optical energy (e.g., light) is lost from the optical waveguide when the light wave reaches the interface between the two materials (the core 215 and the cladding 217) at an angle less than the critical angle ($\theta_c$). The critical angle ($\theta_c$) can be calculated by the following equation:

$$\theta_c=\arcsin(N_1/N_2)$$

Another characteristic of an optical fiber or optical waveguide is the number of modes that are excitable. In an optical waveguide, the term "mode" refers to a specific intensity pattern in a plane transverse to the optical waveguide axis. A close relationship exists between the internal mode pattern and the external speckle pattern of an optical fiber. In a single mode fiber, only one intensity peak is allowed. In multi-mode fibers, a large number of intensity peaks may occur at any location along the waveguide. In any waveguide with circular cross section, the "zero order" mode is formed by light propagating along the waveguide axis (assuming a perfectly straight waveguide). So-called "higher order" modes are formed by light that is not launched in the axial direction, but at some angle to the axis. These modes are guided by the refractive index difference between the core and cladding and each one will usually have lower intensity than the zero order mode. When a step index waveguide is flexed at some location, the lower order and zero order modes become higher order modes because they no longer remain at or near the centerline. In order for light to occupy the higher order modes in a waveguide, either the source of light must be comprised partly of light rays that are at a non-zero angle to the axis (but still within the numerical aperture of the waveguide), or else the waveguide must be coiled or flexed. In general, few higher order modes will exist in a waveguide that is illuminated by a collimated light source, and conversely a large number of higher order modes will exist in a waveguide that is illuminated by a divergent light source.

As can be seen from FIGS. 8A, 8B, 9A, and 9B, the compression and/or flexing of a waveguide preferentially removes the higher order modes, and has relatively less effect on the lower order modes. The sensitivity of the optical system to small compressions and/or small amounts of flexing depend on the availability of a sufficient number of excited waveguide modes. For example, in a case of only five excited modes, theoretically only five different optical power transmission loss levels could be detected, which would produce a rather coarse relationship between deformation and the amount of optical detected by the optical detector of the optical sensing system. On the other hand, if there were 10,000 excited modes, the relationship between deformation and detected optical energy could be much more finely determined and relatively small deformation changes could be detected. Accordingly, in some implementations, the optical source can provide a diverging beam of an NA that is approximately equal to or greater than that of the waveguide. If the light source NA is greater than the waveguide NA, the result is that the portion of the light emitted at the greatest angle of axis escapes into the cladding immediately. The optical waveguide can also be formed so that it is capable of guiding at least 10,000 modes (e.g., greater than 50,000 modes). The number of possible modes in a step index waveguide is given by:

$$N=V^2/2$$

where V is the normalized frequency. The normalized frequency (V) is calculated as follows:

$$V=2\pi a \cdot NA/\lambda,$$

where a is the radius of the core of the optical waveguide, NA is numerical aperture of the waveguide, as discussed above, and $\lambda$ is the wavelength of light. The most practical light sources have a wavelength ($\lambda$) of between 0.7 to 0.85 micrometers. Consequently the product of a and NA must be on the order of 40 micrometers to satisfy the criteria for 50,000 modes. The practical range of NA is 0.2 to 0.4 approximately. Accordingly, a waveguide having an NA of 0.4 would need to have a minimum of a core radius of 100 micrometers to allow for 50,000 modes, and a minimum radius of about 45 micrometers to allow 10,000 modes. In some implementations, the waveguide core 215 has a radius of at least 45 micrometers (e.g., between 150 and 200 micrometers). The optimum size depends in part also on the actual deformation encountered by the waveguide (which is in turn dependent on the waveguide Durometer, the mechanical pressure actually applied to the waveguide, and the amount of flexing of the waveguide). In some implementations, the waveguide can have a soft elastomer core with Shore A Durometer between 45 and 55, an NA between 0.35 and 0.4 (corresponding to a core refractive index of 1.46 and a cladding refractive index of 1.41), and core radius of 150-200 micrometers. This design can produce a 50-70% transmission loss in a short length of waveguide (2-4 cm) when the flexing deformation is from 5-20 degrees over a length of 1-2 cm and/or where the core is compressed by 5-50%.

An NA of 0.2-0.4 can be achieved by having a refractive index difference between core and cladding of 2-4% in common optical grade materials. In light transmission applications, light is introduced into one end of a waveguide. If the waveguide is straight, total internal reflection will cause confinement of all input light that is within the NA of the waveguide, and the loss of light will be minimal. If a waveguide is not straight but has some curvature, some of the light will undergo total internal reflection until it reaches a bend, where it arrives at the core/cladding interface at less than the critical angle ($\theta_c$) and escapes into the cladding. Similarly, if a waveguide is compressed, some of the light will undergo total internal reflection until it reaches a compressed area, where it arrives at the core/cladding interface at less than the critical angle ($\theta_c$) and escapes into the cladding. Variable transmission losses due to pulsatile bending or compression can be measured with an optical detector 240 (e.g., a photosensor) at the optical waveguide exit and used to characterize the pulsatile force acting on the waveguide.

Figure 8A:
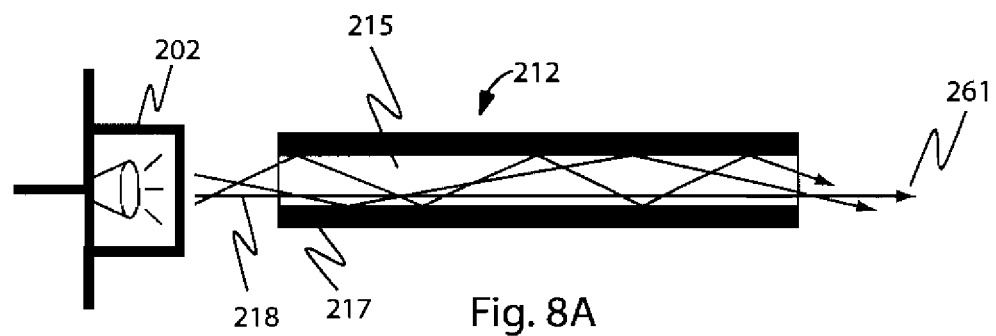
FIGS. 8A and 8B depict how a compressed waveguide results in a reduction in the amount of transmitted light.
Figure 8B:
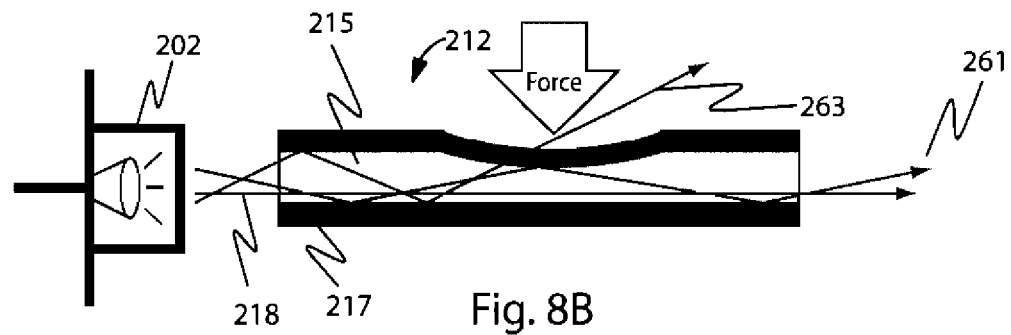
Figure 9A:
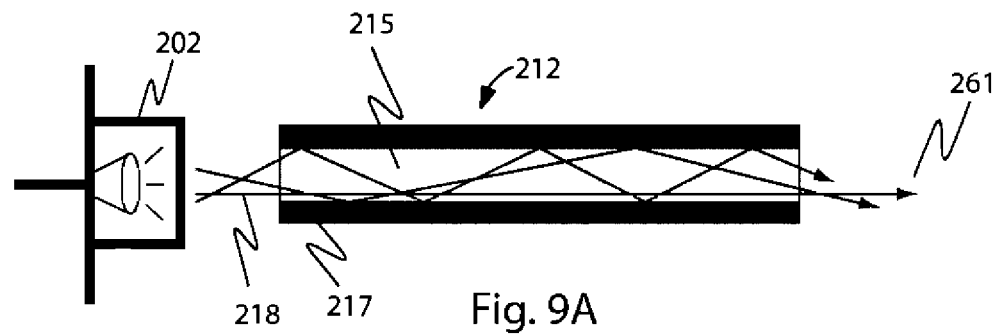
FIGS. 9A and 9B depict how a flexed waveguide results in a reduction in the amount of transmitted light.
Figure 9B:
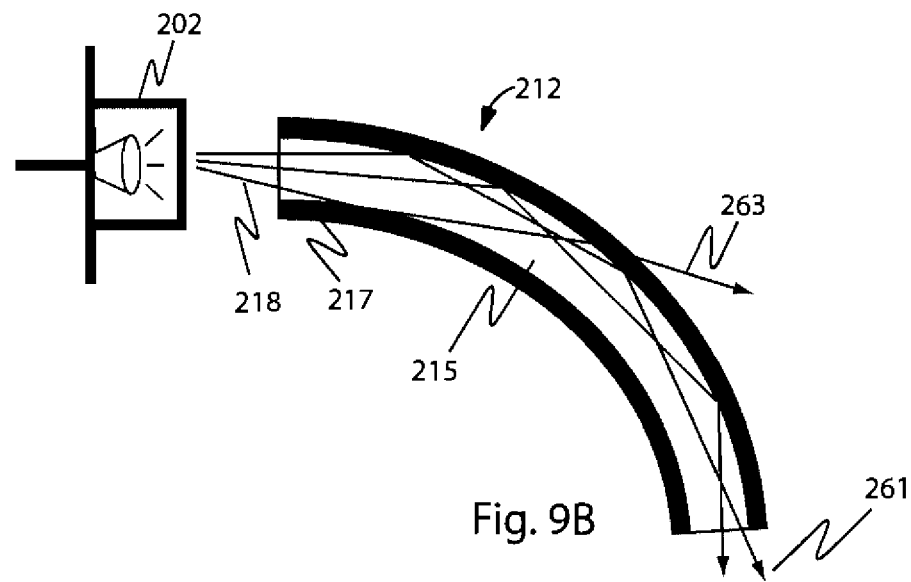

As that shown in FIGS. 8A, 8B, 9A, and 9B, an optical waveguide 212 causes the internal reflection of optical waves 218 within the core of the optical waveguide 212. However, the compression, as shown in FIG. 8B, or the flexing, as shown in FIG. 9B, of the optical waveguide 212 results in a loss of optical energy because the compression or flexing of the optical waveguide 212 results in additional light waves (such as light wave 263) reaching the interface between the core 215 and the cladding 217 at angles less than the critical angle ($\theta_c$). As shown in FIGS. 8A and 8B, the compression of the optical waveguide 212, results in a reduction in the transmitted optical energy 261, because of lost optical energy 263. As shown in FIGS. 9A and 9B, the flexing of the optical waveguide 212, results in a reduction in the transmitted optical energy 261, because of the lost optical energy 263.

The optical waveguide 212 can be flexible and/or compressible. In some implementations, the optical waveguide 212 can include an elastomer. For example, the core 215, the cladding 217, or a combination thereof can include an elastomer. Conventional glass and plastic optical fibers exhibit bending losses, but are generally not deformable to a significant extent by mechanical compression. Compliant waveguides, however, can be fabricated using softer materials. In contrast to glass waveguides, such compliant waveguides may be easily deformed by small compression forces. Examples of suitable elastomers include polysiloxane, polyurethane, and polybutadine rubber. In some implementations, both the core 215 and the cladding 217 include a siloxane elastomer. For example, the optical waveguide can have a cladding 217 composed of silicone elastomer and a core 215 composed of a second silicone elastomer of different refractive index. In some implementations, the cladding elastomer can be a material that does not inhibit the cure of the core material. For example, the cladding elastomer can have addition cure chemistry and the core elastomer can have platinum cure chemistry.

The cladding 217 can be optically clear or can have a translucent appearance. The core 215 can be optically clear. In some embodiments, the cladding can have a refractive index between 1.39 and 1.48 (e.g., between 1.39 and 1.41). In some embodiments, the core 215 can have a refractive index between 1.43 and 1.50 (e.g., between 1.45 and 1.47). The cladding can have a Shore A durometer of between 25 and 75 (e.g., between 45 and 55). The core 215 can have a Shore A durometer of between 25 and 75 (e.g., between 30 and 45).

Figure 10A:
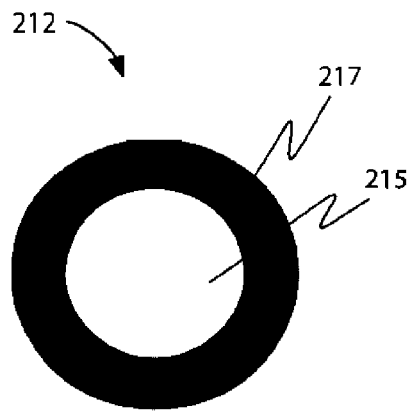
FIGS. 10A-10D are cross-sectional views of different implementations of the waveguide.
Figure 10B:
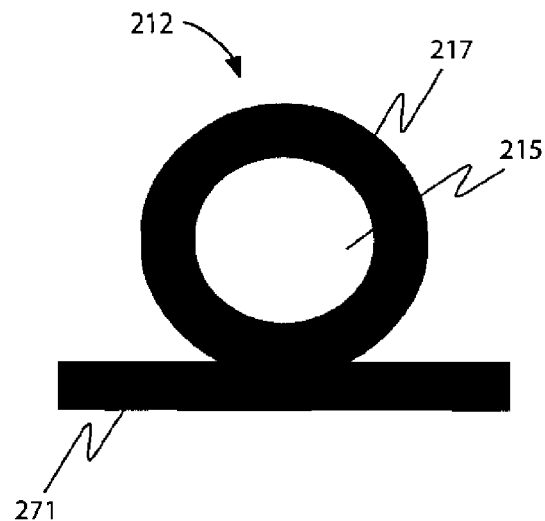
Figure 10C:
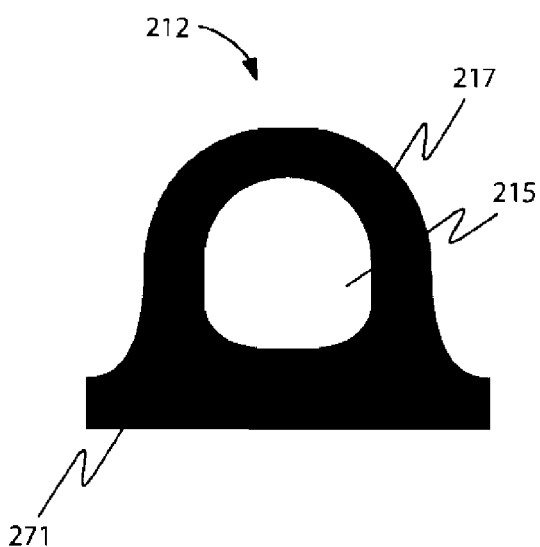
Figure 10D:
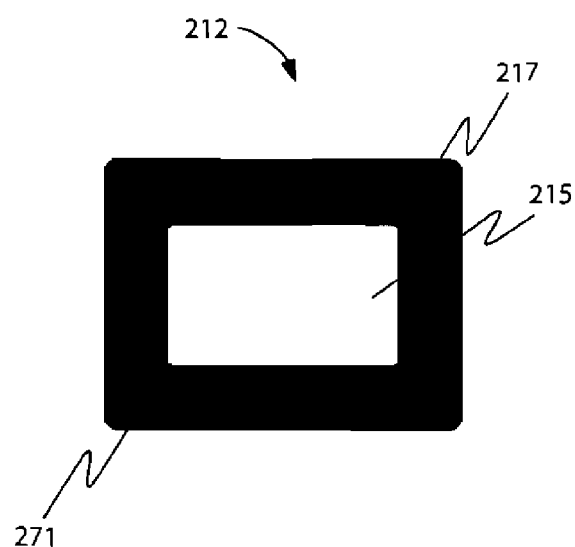

The optical waveguide 212 can have a number of configurations. As shown in FIG. 10A, the cladding 217 can have a circular cross-sectional shape. In some implementations, the cladding can have a flat, widened bearing surface along its length that can serve as an adhesive bonding surface for adhesion of the optical waveguide 212 to a flexible surface, for example, a flexible circuit board used to support the optical waveguide within the optical sensing system. For example, the flat, widened bearing surface can be bonded to a waveguide support surface by a flexible elastomer adhesive. FIGS. 10B-10D show cross-sections of examples of optical waveguides 212 having a flat, widened bearing surface 271.

The cladding 217 of the optical waveguide 212 can be formed by an extrusion process. In some implementations, the core 215 and the cladding 217 can be formed in a co-extrusion process. In some implementations, the cladding 217 can be extruded in a first process to produce a constant cross-sectional shape defining a hollow lumen. The core 215 can then be made by filling the lumen of the cladding 217 with a core material. For example, an extrusion process can be used to make any of the cladding cross-sectional shapes shown in FIGS. 10A-10D. In some implementations, the location of the core centerline may be set to match the location of the exit beam of the optical source 202, after the optical source 202 and optical waveguide 212 are mounted on the flexible waveguide support 235, thereby facilitating ease of optical alignment of the optical waveguide 212 to the optical source 202.

Analytical Methods

Figure 11:
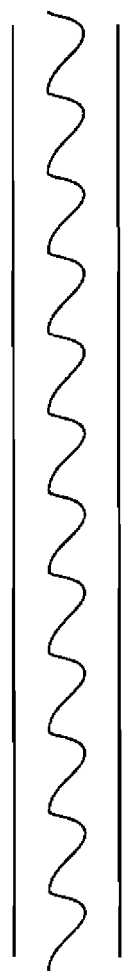
FIG. 11 depicts the pulsatile light transmission in a waveguide subjected to an oscillating deformation due to an arterial pulse.

The optical detector 240 of an optical sensing system 104 can generate an electrical signal 420 indicating the amount of light received. The electrical signal 420 can be a function of time. The electrical optical detector signal 420 is analyzed to determine a number of vital signs. The output unit 106 can determine the amplitude and/or magnitude of each arterial pulse to determine one or more vital signs. In some implementations, the amplitudes and/or magnitudes for a series of arterial pulses can be determined to determine one or more vital signs. In some implementations, the time interval between pulses can be measured during a series of detected arterial pulses and used to determine heart rate. For example, FIG. 11 demonstrates the pulsatile light transmission in a waveguide subjected to an oscillating deformation due to an arterial pulse. Some vital sign measurements, such as a heart rate, do not require input regarding the pressure applied to the anatomical location by, for example, a pneumatic cuff.

Blood pressure, for example, can be measured by placing the cuff (e.g., as shown in FIG. 4) on a patient's arm; inflating the cuff to a pressure at least 10 mmHg higher than the patient's systolic pressure; gradually deflating the cuff pressure to a pressure at least 10 mmHg below diastolic pressure; recording the arterial pulse waveforms produced by the optical sensing system 104; analyzing the waveforms to determine one or more features that correspond to systolic pressure; further analyzing the waveforms to determine one or more features that correspond to diastolic pressure; fully deflating the cuff; and displaying the systolic and diastolic pressure. In some implementations, the waveforms can be recorded both during inflation and deflation of the cuff and both waveforms be used to determine systolic and/or diastolic pressure.

By observing the arterial waveform formed through this process, various vital signs can be determined and/or estimated, such as systolic pressure, diastolic pressure, and mean arterial pressure. In some implementations, the method of measuring blood pressure can include analyzing the arterial pulse waveforms by measuring the amplitudes of the sequence of waveforms recorded during the cuff deflation; determining the cuff pressure at which the pulse waveform amplitude is significantly higher than the waveform amplitude of the preceding pulse occurring at higher cuff pressure during deflation of the cuff; and displaying that pressure as the systolic pressure.

Systolic pressure can be determined in a number of ways based on the data received from the optical sensing system 104 and from data from the sensor fixation device 102. In some implementations, the systolic pressure can be determined at the cuff pressure at which the pulse waveform amplitude is significantly lower than the waveform amplitude of the preceding pulse occurring at lower cuff pressure during inflation of the cuff. In some implementations, the diastolic pressure can be determined during deflation of the cuff at the cuff pressure where the pulse waveform is indicative of the pulsatile action of the arterial segment under the sensor. More specifically, the diastolic pressure can be determined where the pulse waveform first indicates that the artery does not fully close at any time during the cardiac cycle. Different methods of waveform analysis are also possible. A patient's systolic blood pressure can also be continuously monitored by measuring the baseline systolic pressure by one of the methods described above and then pressurizing the cuff to a constant pressure and then continuously monitoring the waveform. The constant pressure can be determined by the previously measured blood pressure reading (e.g., peak arterial pressure). A first measured arterial pulse amplitude can then be used as a reference pulse amplitude and subsequent pulse amplitudes can be compared to that reference pulse amplitude to estimate changes in blood pressure. In some implementations, the pulse waveform morphology can be determined for pulses while the cuff is held at the constant pressure. The pulse waveform morphology can be measured continuously and used to monitor blood pressure changes relative to a baseline value.

In some implementations, such as shown in FIG. 12 the output unit 106 can determine a vital sign by one or more of the above described techniques. For example, the output unit 106 can determine an amplitude, a magnitude and/or a waveform of one or more arterial pulses in a waveform generator 436. In some implementations, the output unit 106 can include a systolic pressure calculator 442 to determine a systolic pressure for a subject based upon a determined amplitude, magnitude and/or waveform and a pressure applied to the subject, which can be detected (e.g., a pressure detected in an inflatable cuff by a pressure sensor). In some implementations, the output unit 106 can include a diastolic pressure calculator 444 to determine a diastolic pressure for a subject based upon a determined amplitude, magnitude and/ or waveform and a pressure applied to the subject, which can be detected (e.g., a pressure detected in an inflatable cuff by a pressure sensor 128). In some implementations, a heart rate calculator 446 can determine a heart rate from either a determined arterial pulse waveform from the optical signal or from pressures detected in an inflatable cuff by a pressure sensor 128.

The output unit 106 shown in FIG. 12, also includes a pressure sensor 128 pneumatically connected to a bladder in the cuff, which transmits data regarding the pressure in the cuff as a function of time to the analog-to-digital converter 435. In some implementations, the output unit 106 can generate a pulse waveform as a function of cuff pressure. The output unit 106 shown in FIG. 12 also includes an inflation controller 452, which can control the inflation and deflation means of the cuff to control the operation of the device. In some implementations, the output unit 106 can dynamically adjust the inflation and deflation of the cuff based on detect arterial pulse characteristics.

A number of implementations have been described. Nevertheless, it will be understood that various modifications can be made without departing from the spirit and scope of the invention. Accordingly, other implementations are within the scope of the following claims.

What is claimed is:

1. An optical motion sensing device comprising:
a sensor frame defining an opening;
a sensor pad disposed in the opening;
an optical sensing system adapted to detect an amount of movement of the sensor pad in the sensor frame, the optical sensing system comprising:
(a) an optical waveguide positioned within the sensor frame such that the movement of the sensor pad results in the flexing or compressing of the optical waveguide,
(b) an optical source device to supply optical energy to a first end of the optical waveguide, and
(c) an optical detector to detect an amount of optical energy exiting a second end of the optical waveguide;
a load spring attached to at least a portion of the sensor frame and also supporting the sensor pad, and configured to counter at least some of a pressure exerted against the sensor pad, and further adapted to allow a desirable displacement of the sensor pad at a maximum pressure; and
an output unit configured to receive a signal indicative of the amount of optical energy exiting the optical waveguide and to generate a measure of the amount of movement of the sensor pad from the received signal.

2. The optical motion sensing device of claim 1, wherein the load spring is adapted to provide a maximum displacement of the sensor pad between 0.5 and 3 millimeters at a maximum pressure.

3. The optical motion sensing device of claim 1, wherein the optical waveguide comprises a siloxane elastomer.

4. The optical motion sensing device of claim 1, wherein the optical waveguide comprises an elastomer selected from the group consisting of polysiloxane, polyurethane, polybutadine rubber, and combinations thereof.

5. An optical motion sensing device comprising:
a sensor frame defining an opening;
a sensor pad disposed in the opening;
an optical sensing system adapted to detect an amount of movement of the sensor pad in the sensor frame, the optical sensing system comprising;
(a) an optical waveguide positioned within the sensor frame such that the movement of the sensor pad results in the flexing or compressing of the optical waveguide, the optical waveguide comprising a numerical aperture of between 0.2 and 0.4,
(b) an optical source device to supply optical energy to a first end of the optical waveguide
(c) an optical detector to detect an amount of optical energy exiting a second end of the optical waveguide; and
an output unit configured to receive a signal indicative of the amount of optical energy exiting the optical waveguide and to generate a measure of the amount of movement of the sensor pad from the received signal.

6. An optical motion sensing device comprising:
a sensor frame defining an opening;
a sensor pad disposed in the opening;
an optical sensing system adapted to detect an amount of movement of the sensor pad in the sensor frame, the optical sensing system comprising:
(a) an optical waveguide positioned within the sensor frame such that the movement of the sensor pad results in the flexing or compressing of the optical waveguide, the optical waveguide comprising a core and a cladding, the core having a refractive index between 1.43 and 1.50, the cladding having a refractive index between 1.39 and 1.48,
(b) an optical source device to supply optical energy to a first end of the optical waveguide
(c) an optical detector to detect an amount of optical energy exiting a second end of the optical waveguide; and
an output unit configured to receive a signal indicative of the amount of optical energy exiting the optical waveguide and to generate a measure of the amount of movement of the sensor pad from the received signal.

7. The optical motion sensing device of claim 6, wherein the core, the cladding, or both the core and the cladding have a Shore A hardness of between 25 and 75.

8. The optical motion sensing device of claim 1, further comprising a waveguide support structure comprising a non-compliant surface, the waveguide support supporting at least a portion of the optical waveguide.

9. An optical motion sensing device comprising:
a sensor frame defining an opening;
a sensor pad disposed in the opening;
an optical sensing system adapted to detect an amount of movement of the sensor pad in the sensor frame, the optical sensing system comprising:

(a) an optical waveguide positioned within the sensor frame such that the movement of the sensor pad results in the flexing or compressing of the optical waveguide,
(b) an optical source device to supply optical energy to a first end of the optical waveguide, and
(c) an optical detector to detect an amount of optical energy exiting a second end of the optical waveguide;
a waveguide support structure comprising a non-compliant surface, the waveguide support supporting at least a portion of the optical waveguide, wherein the optical sensing system is further adapted for the movement of the sensor pad to cause a flexural deformation in an unsupported portion of the optical waveguide in response to an arterial pulse; and
an output unit configured to receive a signal indicative of the amount of optical energy exiting the optical waveguide and to generate a measure of the amount of movement of the sensor pad from the received signal.

10. The optical motion sensing device of claim 1, further comprising a flexible and incompressible support surface that supports the optical waveguide over substantially all of its length.

11. An optical motion sensing device comprising:
a sensor frame defining an opening;
a sensor pad disposed in the opening;
an optical sensing system adapted to detect an amount of movement of the sensor pad in the sensor frame, the optical sensing system comprising:
(a) an optical waveguide positioned within the sensor frame such that the movement of the sensor pad results in the flexing or compressing of the optical waveguide,
(b) an optical source device to supply optical energy to a first end of the optical waveguide, and
(c) an optical detector to detect an amount of optical energy exiting a second end of the optical waveguide;
a flexible and incompressible support surface that supports the optical waveguide over substantially all of its length, wherein the waveguide support surface is a flexible electronic circuit board, to which the waveguide is bonded with a flexible elastomer adhesive; and
an output unit configured to receive a signal indicative of the amount of optical energy exiting the optical waveguide and to generate a measure of the amount of movement of the sensor pad from the received signal.

12. An optical motion sensing device comprising:
a sensor frame defining an opening;
a sensor pad disposed in the opening;
an optical sensing system adapted to detect an amount of movement of the sensor pad in the sensor frame, the optical sensing system comprising:
(a) an optical waveguide positioned within the sensor frame such that the movement of the sensor pad results in the flexing or compressing of the optical waveguide,
(b) an optical source device to supply optical energy to a first end of the optical waveguide, and
(c) an optical detector to detect an amount of optical energy exiting a second end of the optical waveguide;
a flexible and incompressible support surface that supports the optical waveguide over substantially all of its length, wherein the optical source device and the optical detector are mounted on the surface of the waveguide support; and
an output unit configured to receive a signal indicative of the amount of optical energy exiting the optical waveguide and to generate a measure of the amount of movement of the sensor pad from the received signal.

13. An optical motion sensing device comprising:
a sensor frame defining an opening;
a sensor pad disposed in the opening;
an optical sensing system adapted to detect an amount of movement of the sensor pad in the sensor frame, the optical sensing system comprising:
(a) an optical waveguide positioned within the sensor frame such that the movement of the sensor pad results in the flexing or compressing of the optical waveguide,
(b) an optical source device to supply optical energy to a first end of the optical waveguide, and
(c) an optical detector to detect an amount of optical energy exiting a second end of the optical waveguide;
a flexible and incompressible support surface that supports the optical waveguide over substantially all of its length;
a support return element which is configured within the support surface for the optical waveguide and adapted to oppose the flexing of the support surface; and
an output unit configured to receive a signal indicative of the amount of optical energy exiting the optical waveguide and to generate a measure of the amount of movement of the sensor pad from the received signal.

14. The optical motion sensing device of claim 13, wherein the support return element is adapted to provide an increasing contact pressure between the sensor pad and the optical waveguide as the sensor pad moves from a rest position to a position of maximum displacement, with the optical waveguide adapted such that said increasing contact pressure causes a decreasing amount of light exiting the second end of the optical waveguide.

15. An optical motion sensing device comprising:
a sensor frame defining an opening;
a sensor pad disposed in the opening;
an optical sensing system adapted to detect an amount of movement of the sensor pad in the sensor frame, the optical sensing system comprising:
(a) an optical waveguide positioned within the sensor frame such that the movement of the sensor pad results in the flexing or compressing of the optical waveguide,
(b) an optical source device to supply optical energy to a first end of the optical waveguide, and
(c) an optical detector to detect an amount of optical energy exiting a second end of the optical waveguide; and
an output unit configured to receive a signal indicative of the amount of optical energy exiting the optical waveguide and to generate a measure of the amount of movement of the sensor pad from the received signal, wherein the compression and flexing of the optical waveguide when the sensor pad is at the position of maximum contact pressure causes a reduction of 20-80% in the total amount of light exiting the optical waveguide.

16. The optical motion sensing device of claim 15, wherein the compression and flexing of the optical waveguide at the position of maximum contact pressure causes a reduction of 50-70% in the total amount of light exiting the optical waveguide.

17. The optical motion sensing device of claim 1, wherein the optical detector is optically coupled to optical waveguide such that the optical detector receives substantially of the optical energy from the optical source that does not escape from the sides of the sides of the optical waveguide.

18. A compliant waveguide for detecting arterial pulses comprising:
a cladding having a flat surface and defining a lumen, the cladding comprising an elastomer having a Shore A hardness of between 25 and 75; and a core disposed in the lumen, the core comprising an elastomer having a Shore A hardness of between 25 and 75 and a refractive index greater than the refractive index of the cladding.

19. The compliant waveguide of claim 18, wherein the optical waveguide comprises an elastomer selected from the group consisting of polysiloxane, polyurethane, polybutadine rubber, and combinations thereof.

20. The compliant waveguide of claim 18, wherein the cladding has a Shore A durometer of between 45 and 55 and the core has a Shore A hardness between 30 and 45.

21. The compliant waveguide of claim 18, wherein the waveguide is capable of guiding at least 10,000 modes.

22. The compliant waveguide of claim 21, wherein the waveguide is capable of guiding at least 50,000 modes.

23. The compliant waveguide of claim 21, wherein the core has a refractive index between 1.43 and 1.50 and the cladding has a refractive index between 1.39 and 1.48.

24. The compliant waveguide of claim 18, wherein the core has a radius of at least 45 micrometers.

25. The compliant waveguide of claim 18,
wherein the core comprises an elastomer selected from the group consisting of polysiloxane, polyurethane, polybutadine rubber, and combinations thereof, has a Shore A hardness between 30 and 45, has a refractive index between 1.45 and 1.47, and has a radius of between 150 and 200 micrometers;

wherein the cladding has a Shore A durometer of between 45 and 55 and has a refractive index between 1.39 and 1.41; and wherein the waveguide has an NA of between 0.35 and 0.4.

* * * * *

UNITED STATES PATENT AND TRADEMARK OFFICE
CERTIFICATE OF CORRECTION

PATENT NO. : 7,463,796 B2  Page 1 of 1
APPLICATION NO. : 11/944029
DATED : December 9, 2008
INVENTOR(S) : John A. Borgos It is certified that error appears in the above-identified patent and that said Letters Patent is hereby corrected as shown below:

Column 18, line 20 Claim 5, please delete "comprising;" and insert --comprising:-- therefor;

Column 20, line 62 Claim 17, please delete the second occurrence of "sides of the".

Signed and Sealed this

Thirtieth Day of June, 2009

JOHN DOLL
*Acting Director of the United States Patent and Trademark Office*